US008293253B2

(12) United States Patent
Murthy

(10) Patent No.: US 8,293,253 B2
(45) Date of Patent: *Oct. 23, 2012

(54) COMPOSITIONS FOR CONTROLLED DELIVERY OF PHARMACEUTICALLY ACTIVE COMPOUNDS

(75) Inventor: Yerramilli V. S. N. Murthy, Apex, NC (US)

(73) Assignee: IDEXX Laboratories, Inc., Westbrook, ME (US)

( * ) Notice: Subject to any disclaimer, the term of this patent is extended or adjusted under 35 U.S.C. 154(b) by 1213 days.

This patent is subject to a terminal disclaimer.

(21) Appl. No.: 11/259,027

(22) Filed: Oct. 27, 2005

(65) Prior Publication Data
US 2006/0093632 A1 May 4, 2006

Related U.S. Application Data

(60) Provisional application No. 60/638,178, filed on Dec. 23, 2004, provisional application No. 60/622,689, filed on Oct. 28, 2004.

(51) Int. Cl.
A61K 9/00 (2006.01)
A01N 37/12 (2006.01)
(52) U.S. Cl. ........................................ 424/400; 514/561
(58) Field of Classification Search ................... 424/468
See application file for complete search history.

(56) References Cited

U.S. PATENT DOCUMENTS

| 5,270,163 | A | | 12/1993 | Gold et al. |
| 5,332,576 | A | * | 7/1994 | Mantelle ........................ 424/443 |
| 5,332,834 | A | | 7/1994 | Bhattacharya et al. |
| 5,459,127 | A | | 10/1995 | Felgner et al. |
| 5,475,096 | A | | 12/1995 | Gold et al. |
| 5,574,020 | A | | 11/1996 | Klink et al. |
| 5,599,969 | A | | 2/1997 | Hardy et al. |
| 5,629,020 | A | | 5/1997 | Leone-Bay et al. |
| 5,788,983 | A | | 8/1998 | Chien et al. |
| 5,877,212 | A | | 3/1999 | Yu et al. |
| 6,096,813 | A | | 8/2000 | Schimmel et al. |
| 6,464,987 | B1 | | 10/2002 | Fanara et al. |
| 6,887,487 | B2 | | 5/2005 | Murthy et al. |
| 6,946,137 | B2 | | 9/2005 | Murthy et al. |
| 7,038,026 | B2 | | 5/2006 | Crouzet et al. |
| 7,056,704 | B2 | | 6/2006 | Tuschl et al. |
| 7,078,196 | B2 | | 7/2006 | Tuschl et al. |
| 2003/0165434 | A1 | | 9/2003 | Reinhard et al. |
| 2004/0191763 | A1 | | 9/2004 | Delaney et al. |
| 2004/0197408 | A1 | | 10/2004 | Gravett |
| 2004/0220264 | A1 | | 11/2004 | Yu et al. |
| 2005/0124565 | A1 | | 6/2005 | Diener et al. |
| 2005/0175708 | A1 | | 8/2005 | Carrasquillo et al. |
| 2005/0192348 | A1 | | 9/2005 | Bar-Or et al. |
| 2006/0122144 | A1 | | 6/2006 | Kane et al. |
| 2006/0167088 | A1 | | 7/2006 | Widder et al. |
| 2007/0111969 | A1 | * | 5/2007 | Murthy ............................ 514/78 |

FOREIGN PATENT DOCUMENTS

| WO | WO 03/034988 | | 5/2003 |
| WO | WO2004089239 | * | 10/2004 |
| WO | WO2005000241 | * | 1/2005 |

OTHER PUBLICATIONS

Griffin, et al., *The Discovery and Characterization of a Novel Nucleotide-Based Thrombin*, Gene 137 (1993), pp. 25-31.
Jenison, et al., *Oligonucleotide Inhibitors of P-Selection-Dependent Neutrophil-Platelet Adhesion*, Antisense & Nucleic Acid Drug Development, vol. 8 (4): 265-279 (1998).
Bell, et al., *Oligonucleotide NX1838 Inhibits VEGF $_{165}$-Mediated Cellular Responses in Vitro*, In Vitro Cellular & Development Biology, Journal of the Society for In Vitro Biology, vol. 35(9), pp. 533-542 (1999).
Watson, et al., *Anti-L-Selectin Aptamers: Binding Characteristics, Pharmacokinetic Parameters, and Activity Against an Intravascular Target In Vivo*, Antisense & Nucleic Acid Drug Development, 10:63-75 (2000), p. 63.
Daniels, et al., *Generation of RNA Aptamers to the G-Protein-Coupled Receptor for Neurotensin*, NTS-1, Analytical Biochemistry 305, pp. 214-226 (2002).
Chen, et al., *Inhibition of Heregulin Signaling by an Aptamer that Preferably Binds to the Oligomeric Form of Human Epidermal Growth Factor Receptor-3*, Proc. Natl. Acad. Sci. U.S.A. 100(16), pp. 9226-9231, PNAS, Aug. 5, 2003.
Khati, et al., *Neutralization of Infectivity of Diverse R5 Clinical Isolates of Human Immunodeficiency Virus Type 1 by gp120-Binding 2'F-RNA Aptamers*, Journal of Virology, Dec. 2003, pp. 12692-12698.
Vaish, et al., *A Novel, Modification-Dependent ATP-Binding Aptamer Selected from an RNA Library Incorporating a Cationic Functionality*, Biochemistry, 2003, 42, pp. 8842-8851.
Ellington, et al., *In Vitro Selection of RNA Molecules that Bind Specific Ligands*, Nature, vol. 346, Aug. 30, 1990, pp. 818-822.
Tuerk, et al., *Systematic Evolution of Ligands by Exponential Enrichment: RNA Ligands to Bacteriophage T4 DNA Polymerase*, Aug. 3, 1990, Science, vol. 249, pp. 505-510.
Wlotzka, et al., *In Vivo Properties of an Anti GnRH Spiegelmer: An example of an Oligonucleotide-Based Therapeutic Substance Class*, (2002) Proc. Natl. Acad. Sci. U.S.A. 99 (13): pp. 8898-8902. Reyderman, et al. (1998), *Pharmacokinetics and Biodistribution of a Nucleotide-Based Thrombin Inhibitor in Rats*, Pharmaceutical Research, vol. 15, No. 6, 1998, pp. 904-910.
Tucker, et al., *Detection and Plasma Pharmacokinetics of an Anti-Vascular Endothelian Growth Factor Oligonucleotide-Aptamer (NX1838) in Rhesus Monkeys*, Journal of Chromatography B, 732 (1999), pp. 203-212.
Green, et al., *Nuclease-Resistant Nucleic Acid Ligands to Vascular Permeability Factor/Vascular Endothelial Growth Factor*, Chem. & Biol. 2(10), pp. 683-695, 1995.
Jellinek, et al., *Potent 2'-Amino 2'-Deoxypyrimidine RNA Inhibitors of Basic Fibroblast Growth Factor*, Biochemistry 1995, 34, pp. 11363-11372.

(Continued)

Primary Examiner — David J Blanchard
Assistant Examiner — Rachael E Bredefeld
(74) Attorney, Agent, or Firm — Haynes and Boone, LLP

(57) ABSTRACT

The invention relates to pharmaceutical compositions that provide sustained-release of a pharmaceutically active compound and to methods of treating or preventing a condition in an animal by administering the pharmaceutical compositions to the animal by injection. When the pharmaceutical compositions are administered to an animal by injection, they form a drug depot that releases the pharmaceutically active compound over time. The pharmaceutical compositions can also be administered orally.

17 Claims, 3 Drawing Sheets

OTHER PUBLICATIONS

Ruckman, et al., *2'-Fluropyrimidine RNA-Based Aptamers to the 165-Amino Acid Form of Vascular Endothelial Growth Factor (VEGH$_{165}$)*, The Journal of Biological Chemistry, vol. 273, No. 32, Issue of Aug. 7, 1998, pp. 20556-20567.

Uhlmann, et al., *Use of Minimally Modified Antisense Oligonucleotides for Specific Inhibition of Gene Expression, in Methods in Enzymology, Antisense Technology, Part A, General Methods, Methods of Delivery, and RNA Studies*, vol. 313, *edited by M. Ian Phillips, Academic Press*, San Diego, pp. 268-284 (2000).

Burmeister, et al., *Direct In Vitro Selection of a 2'-O-Methyl-Aptamer to VEGF*, Chemistry and Biology, vol. 12, pp. 25-33, Jan. 2005.

Search Report and Written Opinion corresponding to PCT/US 08/69951 application dated Dec. 4, 2008.

Search Report corresponding to PCT/US 05/34415 application dated Apr. 4, 2006.

S. M. Elbashir et al., Genes Dev. 15 (2001) pp. 188-200.

N. Mahanthappa, Pharmacogenomics, 6(8) 2005, pp. 879-883.

D. Bumcrot et al., Nature Chemical Biology, 2(12) 2006, pp. 711-719.

Karkare et al., Appl. Biochem Biotech. 119 (1) 2004, pp. 1-12.

* cited by examiner

US 8,293,253 B2

COMPOSITIONS FOR CONTROLLED DELIVERY OF PHARMACEUTICALLY ACTIVE COMPOUNDS

1. CROSS REFERENCE TO RELATED APPLICATIONS

This application claims the benefit of U.S. provisional application No. 60/638,178, filed Dec. 23, 2004, and U.S. provisional application No. 60/622,689, filed Oct. 28, 2004, the contents of which are expressly incorporated herein.

2. STATEMENT REGARDING FEDERALLY SPONSORED RESEARCH OR DEVELOPMENT

Not Applicable.

3. INCORPORATION BY REFERENCE OF MATERIAL SUBMITTED ON A COMPACT DISC

Not Applicable.

4. FIELD OF THE INVENTION

The invention relates to sustained-release pharmaceutical compositions and to methods of administering pharmaceutically active compounds to an animal using the sustained-release pharmaceutical compositions.

5. BACKGROUND OF THE INVENTION

It is often desirable to administer drugs using controlled- or sustained-release formulations that can maintain therapeutic blood levels of the drug over extended periods of time. These controlled release formulations reduce the frequency of dosing, for enhanced convenience and compliance, and also reduce the severity and frequency of side effects. By maintaining substantially constant blood levels and avoiding blood level fluctuations of the drug, such as are associated with conventional immediate release formulations that are administered several times a day, controlled- or sustained-release formulations can provide a better therapeutic profile than is obtainable with conventional immediate release formulations.

Known methods for controlled- or sustained-drug release include implanted devices, such as osmotic pumps, and drug dispersed in a biocompatible polymer matrix, which can be implanted, administered orally, or injected. Examples of biocompatible polymers used in such applications include poly (lactic acid) and poly(lactic acid-co-glycolic acid). The polymer typically undergoes slow hydrolysis in vivo to continually release the entrapped drug over time. The polymer degradation products are non-toxic and absorbed or metabolized by the body. For example, when the biocompatible polymer is poly(lactic acid) or poly(lactic acid-co-glycolic acid), the degradation products are the parent acids, lactic acid and glycolic acid, which are absorbed by the body.

U.S. Pat. Nos. 6,887,487 and 6,946,137 disclose compositions of a salt of a pharmacologically active compound and a lipophilic counterion and a pharmaceutically acceptable water soluble solvent that are combined together to provide an injectable composition. When injected into an animal at least a part of the composition precipitates to form a depot that slowly releases the pharmacologically active compound over time.

U.S. patent application no. US 2004/0220264 discloses compositions, methods of making the compositions, and uses of compositions that include a molecular complex between an acidic pharmaceutical drug and a functional substance. The functional substance can be an alkaline amino acid, an amino acid amide, an amino acid ester, or a related amino acid. The compositions are allegedly useful for delivering the drug into cutaneous tissue.

U.S. patent application no. US 2004/0197408 discloses formulations of a diblock copolymer having a hydrophobic block and hydrophilic block, an additive selected from an amino acid, and an oligopeptide. The formulations, when admixed with water, form drug delivery vehicles in micellar form.

There remains a need in the art, however, for drug containing pharmaceutical compositions, suitable for injection or implantation, wherein the formulation provides controlled- or sustained-release of the drug.

Citation of any reference in Section 5 of this application is not to be construed that such reference is prior art to the present application.

6. SUMMARY OF THE INVENTION

The invention relates to a pharmaceutical composition comprising (i) an amino acid ester or an amino acid amide, (ii) an acidic pharmaceutically active compound, and (iii) a pharmaceutically acceptable organic solvent, wherein the pharmaceutical composition is injectable and forms a precipitate when injected into water. In one embodiment, the pharmaceutical composition comprises an amino acid ester. In one embodiment, the pharmaceutical composition comprises an amino acid amide.

The invention further relates to a pharmaceutical composition comprising (i) an amino acid ester or amino acid amide, (ii) a carboxylic acid, (iii) a neutral pharmaceutically active compound or a pharmaceutically acceptable salt of a pharmaceutically active compound, and (iv) a pharmaceutically acceptable organic solvent, wherein the pharmaceutical composition is injectable and forms a precipitate when injected into water. In one embodiment, the pharmaceutical composition comprises an amino acid ester. In one embodiment, the pharmaceutical composition comprises an amino acid amide.

The invention further relates to a pharmaceutical composition comprising (i) an N-acyl amino acid, (ii) a basic pharmaceutically active compound, and (iii) a pharmaceutically acceptable organic solvent, wherein the pharmaceutical composition is injectable and forms a precipitate when injected into water.

The invention further relates to methods of treating a condition in an animal comprising administering to an animal in need thereof a pharmaceutical composition of the invention.

7. BRIEF DESCRIPTION OF THE DRAWINGS

FIG. 1 shows the percent of flunixin released as a function of time for various flunixin formulations. (▲) represents the percent of flunixin released from a composition containing a salt of flunixin and tryptophan octanoate, (■) represents the percent of flunixin released from a composition containing a salt of flunixin and tryptophan butanoate, and (♦) represents the percent of flunixin released from a composition containing free flunixin dissolved in N-methylpyrrolidone.

8. DETAILED DESCRIPTION OF THE INVENTION

Figure 1:
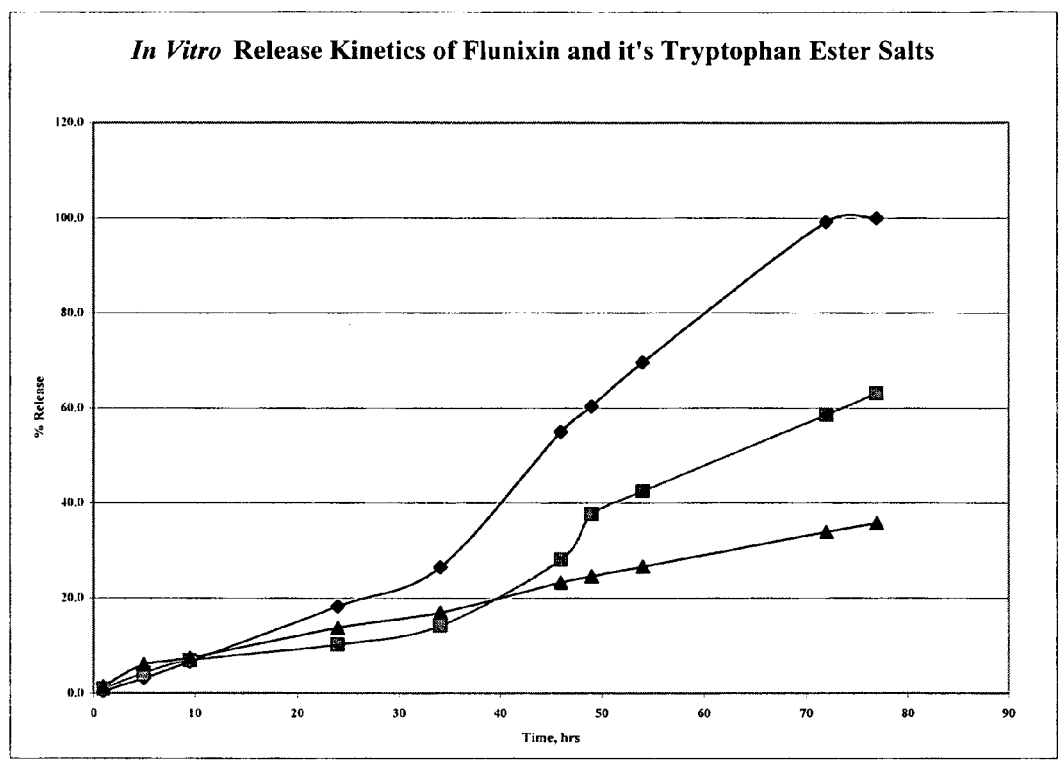

The invention relates to pharmaceutical compositions for administering pharmaceutically active compounds. The compositions provide sustained- or controlled-release of the pharmaceutically active compound. The invention further relates to methods of treating a condition in an animal comprising administering to an animal in need thereof a pharmaceutical composition of the invention.

The invention relates to a pharmaceutical composition comprising (i) an amino acid ester or an amino acid amide and (ii) an acidic pharmaceutically active compound. In one embodiment, the pharmaceutical composition comprises an amino acid ester. In one embodiment, the pharmaceutical composition comprises an amino acid amide. In one embodiment, the pharmaceutical composition is a solid.

In one embodiment, the pharmaceutical composition further comprises a pharmaceutically acceptable organic solvent. Accordingly, the invention further relates to a pharmaceutical composition comprising (i) an amino acid ester or an amino acid amide, (ii) an acidic pharmaceutically active compound, and (iii) a pharmaceutically acceptable organic solvent. In one embodiment, the pharmaceutical composition comprises an amino acid ester. In one embodiment, the pharmaceutical composition comprises an amino acid amide. In one embodiment, the pharmaceutical composition further comprising a pharmaceutically acceptable organic solvent comprises a suspension of solid particles in the pharmaceutically acceptable organic solvent. In one embodiment, the pharmaceutical composition further comprising a pharmaceutically acceptable organic solvent is injectable and forms a precipitate when injected into water.

The invention further relates to a pharmaceutical composition comprising (i) an amino acid ester or amino acid amide, (ii) a carboxylic acid, and (iii) a neutral pharmaceutically active compound or a pharmaceutically acceptable salt of a pharmaceutically active compound. In one embodiment, the pharmaceutical composition comprises an amino acid ester. In one embodiment, the pharmaceutical composition comprises an amino acid amide. In one embodiment, the pharmaceutical composition is a solid.

In one embodiment, the pharmaceutical composition further comprises a pharmaceutically acceptable organic solvent. Accordingly, the invention further relates to a pharmaceutical composition comprising (i) an amino acid ester or amino acid amide, (ii) a carboxylic acid, (iii) a neutral pharmaceutically active compound or a pharmaceutically acceptable salt of a pharmaceutically active compound, and (iv) a pharmaceutically acceptable organic solvent. In one embodiment, the pharmaceutical composition comprises an amino acid ester. In one embodiment, the pharmaceutical composition comprises an amino acid amide. In one embodiment, the pharmaceutical composition further comprising a pharmaceutically acceptable organic solvent comprises a suspension of solid particles in the pharmaceutically acceptable organic solvent. In one embodiment, the pharmaceutical composition further comprising a pharmaceutically acceptable organic solvent is injectable and forms a precipitate when injected into water.

The invention further relates to a pharmaceutical composition comprising (i) an N-acyl amino acid and (ii) a basic pharmaceutically active compound. In one embodiment, the pharmaceutical composition is a solid.

In one embodiment, the pharmaceutical composition further comprises a pharmaceutically acceptable organic solvent. Accordingly, the invention further relates to a pharmaceutical composition comprising (i) an N-acyl amino acid, (ii) a basic pharmaceutically active compound, and (iii) a pharmaceutically acceptable organic solvent. In one embodiment, the pharmaceutical composition further comprising a pharmaceutically acceptable organic solvent comprises a suspension of solid particles in the pharmaceutically acceptable organic solvent. In one embodiment, the pharmaceutical composition further comprising a pharmaceutically acceptable organic solvent is injectable and forms a precipitate when injected into water.

8.1 Definitions

As used herein, the following terms have the following meaning:

"$C_1$-$C_{22}$ hydrocarbon group" means a straight or branched, saturated or unsaturated, cyclic or non-cyclic, aromatic or non-aromatic, carbocyclic or heterocyclic group having from 1 to 22 carbon atoms. Similarly, "$C_1$-$C_{21}$ hydrocarbon group," "$C_1$-$C_{18}$ hydrocarbon group," "$C_6$-$C_{18}$ hydrocarbon group," "$C_8$-$C_{18}$ hydrocarbon group," and a "$C_{10}$-$C_{18}$ hydrocarbon group" means a straight or branched, saturated or unsaturated, cyclic or non-cyclic, aromatic or non-aromatic, carbocyclic or heterocyclic group having from 1 to 21 carbon atoms, from 1 to 18 carbon atoms, from 6 to 18 carbon atoms, from 8 to 18 carbon atoms, and from 10 to 18 carbon atoms, respectively. Accordingly, the phrase "an acyl group of formula —C(O)—$R_1$, wherein $R_1$ is a $C_1$ to $C_{21}$ group means an acyl group of formula —C(O)—$R_1$, wherein $R_1$ is a straight or branched, saturated or unsaturated, cyclic or non-cyclic, aromatic or non-aromatic, carbocyclic or heterocyclic hydrocarbon group having from 1 to 21 carbon atoms. Representative acyl groups of formula —C(O)—$R_1$, wherein $R_1$ is an unsubstituted $C_1$ to $C_{21}$ group include, but are not limited to, acetyl, propionyl, butanoyl, hexanoyl, caproyl, laurolyl, myristoyl, palmitoyl, stearoyl, palmioleoyl, oleoyl, linoleoyl, linolenoyl, and benzoyl.

The term "salt," as used herein, means two compounds that are not covalently bound but are chemically bound by ionic interactions.

The term "pharmaceutically acceptable organic solvent," as used herein, means an organic solvent that when administered to an animal does not have undue adverse effects such as excessive toxicity, irritation, or allergic response commensurate with a reasonable benefit/risk ratio. Preferably, the pharmaceutically acceptable organic solvent is a solvent that is generally recognized as safe ("GRAS") by the United States Food and Drug Administration ("FDA").

The term "water miscible organic solvent," as used herein, means an organic solvent that is capable of mixing with water in any ratio without separating into two phases.

The term "water soluble organic solvent," as used herein, means an organic solvent that has a significant level of solubility in water. Typically, a water soluble organic solvent is soluble in water in an amount of at least about 5 percent by weight, preferably at least about 10 percent by weight, more preferably at least about 20 percent by weight, and most preferably at least about 50 percent by weight. For example, triacetin is considered a water soluble solvent since it is soluble in water at a ratio of about 1:14.

The phrase "forms a precipitate," as used herein, means that the pharmaceutical composition forms a precipitate, or solid, when injected into water or into a physiological (in vivo) environment. A precipitate is an insoluble solid formed in solution at room temperature in vitro or in a physiological (in vivo) environment. The precipitate can take many forms such as, for example, a solid, a crystal, a gummy mass, or a gel. Preferably, the precipitate is a gummy mass or a gel. A composition of the invention forms a precipitate in water when at least 10% of the composition is retained on a 0.22 μm filter when the composition is mixed with water and filtered at 98° F. Typically, to form the precipitate, about 1 mL of the pharmaceutical composition is injected into about 5 mL of water.

The term "fatty acid," as used herein means a carboxylic acid of formula R—C(O)OH, wherein R a is $C_6$-$C_{22}$ linear or branched, saturated or unsaturated, hydrocarbon group. Representative fatty acids include, but are not limited to, caproic acid, lauric acid, myristic acid, palmitic acid, stearic acid, palmic acid, oleic acid, linoleic acid, and linolenic acid.

The term "fluoroquinolone," as used herein, means any compound having the basic structure:

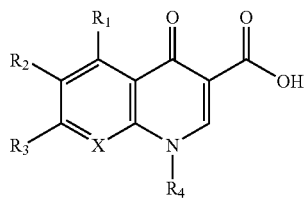

wherein $R_1$, $R_2$, $R_3$, and $R_4$ can be a variety of functional groups and X can be carbon, which may be substituted or unsubstituted, or nitrogen. One skilled in the art would readily recognize fluoroquinolones useful in the compositions and methods of the invention. Typically, the fluoroquinolones are useful as antibiotics but they may also be used to treat other conditions (for example, nephrotic syndromes).

The phrase "injectable" or "injectable composition," as used herein, means a composition that can be drawn into a syringe and injected subcutaneously, intraperitoneally, or intramuscularly into an animal without causing adverse effects due to the presence of solid material in the composition. Solid materials include, but are not limited to, crystals, gummy masses, and gels. Typically, a formulation or composition is considered to be injectable when no more than 10%, preferably no more than 5%, more preferably no more than 2%, and most preferably no more than 1% of the formulation is retained on a 0.22 μm filter when the formulation is filtered through the filter at 98° F.

The term "suspension," as used herein, means solid particles that are evenly dispersed in a solvent, which can be aqueous or non-aqueous. In one embodiment, the particles have an average particle size of less than about 100 μm determined using a particle size analyzer such as commercially available from Microtrac Inc. of Montgomeryville, Pa.

The term "animal," as used herein, includes, but is not limited to, humans, canines, felines, equines, bovines, ovines, porcines, amphibians, reptiles, and avians. Representative animals include, but are not limited to a cow, a horse, a sheep, a pig, an ungulate, a chimpanzee, a monkey, a baboon, a chicken, a turkey, a mouse, a rabbit, a rat, a guinea pig, a dog, a cat, and a human. In one embodiment, the animal is a mammal. In one embodiment, the animal is a human. In one embodiment, the animal is a canine, a feline, an equine, a bovine, an ovine, or a porcine.

The term "pharmaceutically active compound," as used herein, means a compound that causes a pharmacological effect in an animal. Typically, the pharmacological effect is treating or preventing a condition in an animal.

The term "condition," as used herein means an interruption, cessation, or disorder of a bodily function, system, or organ. Representative conditions include, but are not limited to, infections such as bacterial, viral, fungal and, parasitic infections; diseases such as cancer; inflammation; diabetes; and organ failure.

The term "effective amount," as used herein, means an amount sufficient to treat or prevent a condition in an animal.

The phrase "treating," "treatment of," and the like includes the amelioration or cessation of a specified condition.

The phrase "preventing," "prevention of," and the like include the avoidance of the onset of a condition.

The phrase "drug depot," as used herein means a precipitate that includes the pharmaceutically active compound formed within the body of a treated animal that releases a pharmaceutically effective amount of the pharmaceutically active compound over time.

The phrase "neutral pharmaceutically active compound," as used herein means a pharmaceutically active compound that has no net charge. Neutral pharmaceutically active compounds include zwitterions.

The phrase "acidic pharmaceutically active compound," as used herein means a pharmaceutically active compound that has an acidic functional group, i.e., a group that is capable of donating a proton to a basic functional group such as an amine group. Representative acidic functional group include, but are not limited to —COOH (i.e., carboxylic acid groups), —S(O)$_2$ —OH (i.e., sulfonic acid groups), —OP(O)(OR)(OH), —O(P)(OH)$_2$, —P(O)(OR)(OH), —(P)(OH)$_2$), —OP(O)(R)(OH), and —P(O)(R)(OH), wherein R is a hydrocarbon group that can optionally be substituted.

The phrase "basic pharmaceutically active compound," as used herein means a pharmaceutically active compound that has a basic functional group, i.e., a group that is capable of accepting a proton from an acidic functional group such as a carboxylic acid group. A representative basic functional group is an amine group.

The phrase "pharmaceutically acceptable salt," as used herein, is a salt formed from an acid and a basic group of a pharmaceutically active compounds. Illustrative salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. The term "pharmaceutically acceptable salt" also refers to a salt prepared from a pharmaceutically active compound having an acidic functional group, such as a carboxylic acid functional group, and a pharmaceutically acceptable inorganic or organic base. Suitable bases include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or trialkylamines; dicyclohexylamine; tributyl amine; pyridine; N-methyl, N-ethylamine; diethylamine; triethylamine; mono-, bis-, or tris-(2-hydroxy-lower alkyl amines), such as mono-, bis-, or tris-(2-hydroxyethyl)amine, 2-hydroxy-tert-butylamine, or tris-(hydroxymethyl)methylamine, N,N,-di-lower alkyl-N-(hydroxy lower alkyl)-amines, such as N,N,-dimethyl-N-(2-hydroxyethyl)amine, or tri-(2-hydroxyethyl)amine; N-methyl-D-glucamine; and amino acids such as arginine, lysine, and the like.

The phrase "substantially free of," as used herein, means less than about 2 percent by weight, preferably less than about 1 percent by weight, more preferably less than about 0.5 percent by weight, and most preferably less than about 0.2 percent by weight. For example, the phrase "a pharmaceutical composition substantially free of water" means that the amount of water in the pharmaceutical composition is less than about 2 percent by weight of the pharmaceutical composition, preferably less than about 1 percent by weight of the pharmaceutical composition, more preferably less than about 0.5 percent by weight of the pharmaceutical composition, and most preferably less than about 0.2 percent by weight of the pharmaceutical composition.

The term "somatotropin," as used herein, means a polypeptide that has biological activity and chemical structure substantially similar to that of a somatotropin produced in the pituitary gland of an animal. Such somatotropins include natural somatotropins produced by pituitary somatotropic cells and somatotropins expressed by genetically transformed microorganisms such as E. coli, other bacteria, or yeast. Such microorganism produced somatotropins may have an amino acid sequence identical to the natural somatotropin or can be analogs having one or more variations in amino acid sequence which can provide enhanced biological activity or some other advantage. Somatotropins include hormones useful for enhancing lean-to-fat ratio, feed efficiency, and milk production in various mammalian species including, but not limited to, cattle (e.g., dairy cows), sheep, goats and swine. Representative somatotropins include, but are not limited to, natural or microbially expressed bovine, ovine, and porcine somatotropins; bovine, porcine, or other animal prolactins; growth hormone releasing factors; placental lactogens; and insulin-like growth factors.

8.2 The Amino Acid Esters

The amino acid esters can be any ester of any amino acid, i.e., an amino acid wherein the carboxylic acid group of the amino acid is esterified with a $C_1$-$C_{22}$ alcohol. Accordingly, the amino acid esters have the general formula (I):

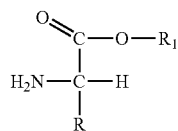

(I)

wherein
R is the amino acid side chain; and
$R_1$ is a $C_1$ to $C_{22}$ hydrocarbon group.

As one of ordinary skill in the art would readily know, a wide variety of groups are possible for the amino acid side, R. For example, the amino acid side can be a hydrocarbon group that can be optionally substituted. Suitable substituents include, but are not limited to, halo, nitro, cyano, thiol, amino, hydroxy, carboxylic acid, sulfonic acid, aromatic group, and aromatic or non-aromatic heterocyclic group. Preferably the amino acid side chain is a $C_1$-$C_{10}$ straight or branched chain hydrocarbon, optionally substituted with a thiol, amino, hydroxy, carboxylic acid, aromatic group, or aromatic or non-aromatic heterocyclic group; an aromatic group, or an aromatic or non-aromatic heterocyclic group.

The amino acid ester can be an ester of a naturally occurring amino acid or a synthetically prepared amino acid. The amino acid can be a D-amino acid or an L-amino acid. Preferably, the amino acid ester is the ester of a naturally occurring amino acid. More, preferably, the amino acid ester is an ester of an amino acid selected from glycine, alanine, valine, leucine, isoleucine, phenylalanine, asparagine, glutamine, tryptophane, proline, serine, threonine, tyrosine, hydroxyproline, cysteine, methionine, aspartic acid, glutamic acid, lysine, arginine, and histidine.

The hydrocarbon group, $R_1$, can be any $C_1$ to $C_{22}$ hydrocarbon group. Representative $C_1$ to $C_{22}$ hydrocarbon groups include, but are not limited to, methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, allyl, cyclopentyl, cyclohexyl, cis-9-hexadecenyl, cis-9-octadecenyl, cis, cis-9,12-octadecenyl, and cis, cis, cis-9, 12, 15-octadecatrienyl.

In one embodiment, $R_1$ is a straight or branched chain, saturated or unsaturated alkyl group.
In one embodiment, $R_1$ is a straight chain alkyl group.
In one embodiment, $R_1$ is a branched chain alkyl group.
In one embodiment, $R_1$ is a saturated alkyl group.
In one embodiment, $R_1$ is an unsaturated alkyl group.
In one embodiment, $R_1$ is a straight chain, saturated alkyl group.
In one embodiment, $R_1$ is a straight chain, unsaturated alkyl group.
In one embodiment, $R_1$ is a $C_6$-$C_{18}$ hydrocarbon group.
In one embodiment, $R_1$ is a $C_8$-$C_{18}$ hydrocarbon group.
In one embodiment, $R_1$ is a $C_{10}$-$C_{18}$ hydrocarbon group.
In one embodiment, $R_1$ is a $C_6$-$C_{18}$ straight chain alkyl group.
In one embodiment, $R_1$ is a $C_6$-$C_{18}$ branched chain alkyl group.
In one embodiment, $R_1$ is a $C_6$-$C_{18}$ saturated alkyl group.
In one embodiment, $R_1$ is a $C_6$-$C_{18}$ unsaturated alkyl group.
In one embodiment, $R_1$ is a $C_8$-$C_{18}$ straight chain alkyl group.
In one embodiment, $R_1$ is a $C_8$-$C_{18}$ branched chain alkyl group.
In one embodiment, $R_1$ is a $C_8$-$C_{18}$ saturated alkyl group.
In one embodiment, $R_1$ is a $C_8$-$C_{18}$ unsaturated alkyl group.
In one embodiment, $R_1$ is a $C_{10}$-$C_{18}$ straight chain alkyl group.
In one embodiment, $R_1$ is a $C_{10}$-$C_{18}$ branched chain alkyl group.
In one embodiment, $R_1$ is a $C_{10}$-$C_{18}$ saturated alkyl group.
In one embodiment, $R_1$ is a $C_{10}$-$C_{18}$ unsaturated alkyl group.

The amino acid esters can be obtained by esterifying an amino acid with an alcohol of formula $R_1$—OH using methods well known to those skilled in the art such as those described in J. March, *Advanced Organic Chemistry, Reaction Mechanisms and Structure*, $4^{th}$ ed. John Wiley & Sons, NY, 1992, pp. 393-400. The amino acids and alcohols of formula $R_1$—OH are commercially available or can be prepared by methods well known to those skilled in the art. When esterifying the amino acid with the alcohol of formula $R_1$—OH, it may be necessary to protect some other functional group of the amino acid or the alcohol with a protecting group that is subsequently removed after the esterification reaction. One of ordinary skill in the art would readily know what functional groups would need to be protected before esterifying the amino acid with the alcohol of formula $R_1$—OH.

Suitable protecting groups are known to those skilled in the art such as those described in T. W. Greene, et al. *Protective Groups in Organic Synthesis*, 3$^{rd}$ ed. (1999).

8.3 The Amino Acid Amides

The amino acid amides can be any amide of any amino acid, i.e., an amino acid wherein the carboxylic acid group of the amino acid is reacted with a $C_1$-$C_{22}$ amine to provide an amide. Accordingly, the amino acid amides have the general formula (I):

$$\underset{\underset{R}{\overset{|}{H_2N-C-H}}}{\overset{O}{\overset{\|}{C}}-\overset{R_3}{\underset{|}{N}}-R_4} \quad (I)$$

wherein
R is the amino acid side chain;
$R_3$ is a $C_1$ to $C_{22}$ hydrocarbon group; and
$R_4$ is hydrogen or a $C_1$ to $C_{22}$ hydrocarbon group.

As one of ordinary skill in the art would readily know, a wide variety of groups are possible for the amino acid side, R. For example, the amino acid side can be a hydrocarbon group that can be optionally substituted. Suitable substituents include, but are not limited to, halo, nitro, cyano, thiol, amino, hydroxy, carboxylic acid, sulfonic acid, aromatic group, and aromatic or non-aromatic heterocyclic group. Preferably the amino acid side chain is a $C_1$-$C_{10}$ straight or branched chain hydrocarbon, optionally substituted with a thiol, amino, hydroxy, carboxylic acid, aromatic group, or aromatic or non-aromatic heterocyclic group; an aromatic group, or an aromatic or non-aromatic heterocyclic group.

The amino acid amide can be an amide of a naturally occurring amino acid or a synthetically prepared amino acid. The amino acid can be a D-amino acid or an L-amino acid. Preferably, the amino acid ester is the ester of a naturally occurring amino acid. More, preferably, the amino acid ester is an ester of an amino acid selected from glycine, alanine, valine, leusine, isoleucine, phenylalanine, asparagine, glutamine, tryptophane, proline, serine, threonine, tyrosine, hydroxyproline, cysteine, methionine, aspartic acid, glutamic acid, lysine, arginine, and histidine.

The $R_3$ group can be any $C_1$ to $C_{22}$ hydrocarbon group. The $R_4$ group can be hydrogen or any $C_1$ to $C_{22}$ hydrocarbon group. Representative $C_1$ to $C_{22}$ hydrocarbon groups include, but are not limited to, methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, allyl, cyclopentyl, cyclohexyl, cis-9-hexadecenyl, cis-9-octadecenyl, cis, cis-9,12-octadecenyl, and cis, cis, cis-9,12,15-octadecatrienyl.

In one embodiment, $R_4$ is hydrogen and $R_3$ is a straight or branched chain, saturated or unsaturated alkyl group.

In one embodiment, $R_4$ is hydrogen and $R_3$ is a straight chain alkyl group.

In one embodiment, $R_4$ is hydrogen and $R_3$ is a branched chain alkyl group.

In one embodiment, $R_4$ is hydrogen and $R_3$ is a saturated alkyl group.

In one embodiment, $R_4$ is hydrogen and $R_3$ is an unsaturated alkyl group.

In one embodiment, $R_4$ is hydrogen and $R_3$ is a straight chain, saturated alkyl group.

In one embodiment, $R_4$ is hydrogen and $R_3$ is a straight chain, unsaturated alkyl group.

In one embodiment, $R_4$ is hydrogen and $R_3$ is a $C_6$-$C_{18}$ hydrocarbon group.

In one embodiment, $R_4$ is hydrogen and $R_3$ is a $C_6$-$C_{18}$ straight chain alkyl group.

In one embodiment, $R_4$ is hydrogen and $R_3$ is a $C_6$-$C_{18}$ branched chain alkyl group.

In one embodiment, $R_4$ is hydrogen and $R_3$ is a $C_6$-$C_{18}$ saturated alkyl group.

In one embodiment, $R_4$ is hydrogen and $R_3$ is an $C_6$-$C_{18}$ unsaturated alkyl group.

In one embodiment, $R_4$ is hydrogen and $R_3$ is a $C_8$-$C_{18}$ hydrocarbon group.

In one embodiment, $R_4$ is hydrogen and $R_3$ is a $C_8$-$C_{18}$ straight chain alkyl group.

In one embodiment, $R_4$ is hydrogen and $R_3$ is a $C_8$-$C_{18}$ branched chain alkyl group.

In one embodiment, $R_4$ is hydrogen and $R_3$ is a $C_8$-$C_{18}$ saturated alkyl group.

In one embodiment, $R_4$ is hydrogen and $R_3$ is an $C_8$-$C_{18}$ unsaturated alkyl group.

In one embodiment, $R_4$ is hydrogen and $R_3$ is a $C_{10}$-$C_{18}$ hydrocarbon group.

In one embodiment, $R_4$ is hydrogen and $R_3$ is a $C_{10}$-$C_{18}$ straight chain alkyl group.

In one embodiment, $R_4$ is hydrogen and $R_3$ is a $C_{10}$-$C_{18}$ branched chain alkyl group.

In one embodiment, $R_4$ is hydrogen and $R_3$ is a $C_{10}$-$C_{18}$ saturated alkyl group.

In one embodiment, $R_4$ is hydrogen and $R_3$ is an $C_{10}$-$C_{18}$ unsaturated alkyl group.

In one embodiment, each of $R_3$ and $R_4$ are a straight or branched chain, saturated or unsaturated alkyl group, wherein $R_3$ and $R_4$ may be the same or different.

In one embodiment, each of $R_3$ and $R_4$ are a $C_6$-$C_{18}$ hydrocarbon group, wherein $R_3$ and $R_4$ may be the same or different.

In one embodiment, each of $R_3$ and $R_4$ are a $C_8$-$C_{18}$ hydrocarbon group, wherein $R_3$ and $R_4$ may be the same or different.

In one embodiment, each of $R_3$ and $R_4$ are a $C_{10}$-$C_{18}$ hydrocarbon group, wherein $R_3$ and $R_4$ may be the same or different.

In one embodiment, the combined number of carbon atoms in $R_3$ and $R_4$ is at least 6. In one embodiment, the combined number of carbon atoms in $R_3$ and $R_4$ is at least 8. In one embodiment, the combined number of carbon atoms in $R_3$ and $R_4$ is at least 10. In one embodiment, the combined number of carbon atoms in $R_3$ and $R_4$ is at least 12.

In one embodiment, the combined number of carbon atoms in $R_3$ and $R_4$ ranges from about 6 to 30. In one embodiment, the combined number of carbon atoms in $R_3$ and $R_4$ ranges from about 8 to 30. In one embodiment, the combined number of carbon atoms in $R_3$ and $R_4$ ranges from about 10 to 30. In one embodiment, the combined number of carbon atoms in $R_3$ and $R_4$ ranges from about 12 to 30. In one embodiment, the combined number of carbon atoms in $R_3$ and $R_4$ ranges from about 6 to 22. In one embodiment, the combined number of carbon atoms in $R_3$ and $R_4$ ranges from about 8 to 22. In one embodiment, the combined number of carbon atoms in $R_3$ and $R_4$ ranges from about 10 to 22. In one embodiment, the combined number of carbon atoms in $R_3$ and $R_4$ ranges from about 12 to 22. In one embodiment, the combined number of carbon atoms in $R_3$ and $R_4$ ranges from about 6 to 18. In one embodiment, the combined number of carbon atoms in $R_3$ and $R_4$ ranges from about 8 to 18. In one embodiment, the combined number of carbon atoms in $R_3$ and $R_4$ ranges from about 10 to 18. In one embodiment, the combined number of carbon atoms in $R_3$ and $R_4$ ranges from about 12 to 18.

The amino acid amides can be obtained by converting the carboxylic acid group of the amino acid to an amide group using methods well known to those skilled in the art such as those described in J. March, *Advanced Organic Chemistry, Reaction Mechanisms and Structure*, 4$^{th}$ ed. John Wiley & Sons, NY, 1992, pp. 417-427. Typically, the amino acid is converted to an amino acid derivative such as an amino acid ester or an acid chloride of the amino acid and the amino acid derivative is then reacted with an amine of formula $NHR_3R_4$ to provide the amino acid amide. The amino acids and amines of formula $NHR_3R_4$ are commercially available or can be prepared by methods well known to those skilled in the art. When forming the derivative of the amino acid or reacting the amino acid derivative with an amine of formula $NHR_3R_4$, it may be necessary to protect some other functional group of the amino acid derivative or the amine with a protecting group that is subsequently removed after the amidation reaction. One of ordinary skill in the art would readily know what functional groups would need to be protected before reacting the derivative of the amino acid with the amine of formula $NHR_3$. Suitable protecting groups are known to those skilled in the art such as those described in T. W. Greene, et al *Protective Groups in Organic Synthesis*, 3$^{rd}$ ed. (1999).

8.4 The Carboxylic Acid

The carboxylic acid can be any pharmaceutically acceptable carboxylic acid. Typically, the carboxylic acid is a $C_1$-$C_{22}$ carboxylic acid. Suitable carboxylic acids include, but are not limited to, acetic acid, propanic acid, butanoic acid, pentanoic acid, decanoic acid, hexanoic acid, benzoic acid, caproic acid, lauric acid, myristic acid, palmitic acid, stearic acid, palmic acid, oleic acid, linoleic acid, and linolenic acid.

In one embodiment, the carboxylic acid is a $C_6$-$C_{22}$ carboxylic acid.

In one embodiment, the carboxylic acid is a $C_8$-$C_{22}$ carboxylic acid.

In one embodiment, the carboxylic acid is a $C_{10}$-$C_{22}$ carboxylic acid.

In one embodiment, the carboxylic acid is a $C_6$-$C_{18}$ carboxylic acid.

In one embodiment, the carboxylic acid is a $C_8$-$C_{18}$ carboxylic acid.

In one embodiment, the carboxylic acid is a $C_{10}$-$C_{18}$ carboxylic acid.

In one embodiment, the carboxylic acid is a saturated or unsaturated fatty acid.

In one embodiment, the carboxylic acid is a saturated fatty acid.

In one embodiment, the carboxylic acid is an unsaturated fatty acid.

In one embodiment, the carboxylic acid is a dicarboxylic acid. Suitable dicarboxylic acids include, but are not limited to, oxalic acid, malonic aid, succinic acid, glutamic acid, adipic acid, and pimelic acid.

The carboxylic acids are commercially available or can be prepared by methods well known to those skilled in the art.

In one embodiment, the carboxylic acid is an N-acyl amino acid. The N-acyl amino acids have the following general formula (II):

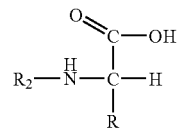

(II)

wherein
R is the amino acid side chain and is defined above; and
$R_2$ is an acyl group of formula —C(O)—$R_5$, wherein $R_5$ is a substituted $C_1$ to $C_{21}$ hydrocarbon group, i.e., the acyl group, $R_2$, is a $C_1$- to $C_{22}$ acyl group. Representative acyl groups of formula —C(O)—$R_5$ include, but are not limited to, acetyl, propionyl, butanoyl, hexanoyl, caproyl, heptoyl, octoyl, nonoyl, decoyl, undecoyl, dodecoyl, tridecoyl, tetradecoyl, pentadecoyl, hexadecoyl, heptadecoyl, octadecoyl, laurolyl, myristoyl, palmitoyl, stearoyl, palmioleoyl, oleoyl, linoleoyl, linolenoyl, and benzoyl.

In one embodiment, $R_5$ is a $C_5$-$C_{21}$ hydrocarbon group, i.e., the acyl group of formula —C(O)—$R_5$ is a $C_6$-$C_{22}$ acyl group.

In one embodiment, $R_5$ is a $C_7$-$C_{21}$ hydrocarbon group, i.e., the acyl group of formula —C(O)—$R_5$ is a $C_8$-$C_{22}$ acyl group.

In one embodiment, $R_5$ is a $C_9$-$C_{21}$ hydrocarbon group, i.e., the acyl group of formula —C(O)—$R_5$ is a $C_{10}$-$C_{22}$ acyl group.

In one embodiment, $R_5$ is a $C_5$-$C_{17}$ hydrocarbon group, i.e., the acyl group of formula —C(O)—$R_5$ is a $C_6$-$C_{18}$ acyl group.

In one embodiment, $R_5$ is a $C_7$-$C_{17}$ hydrocarbon group, i.e., the acyl group of formula —C(O)—$R_5$ is a $C_8$-$C_{18}$ acyl group.

In one embodiment, $R_5$ is a $C_9$-$C_{17}$ hydrocarbon group, i.e., the acyl group of formula —C(O)—$R_5$ is a $C_{10}$-$C_{18}$ acyl group.

In one embodiment, the acyl group of formula —C(O)—$R_5$ is obtained from a saturated or unsaturated fatty acid.

In one embodiment, the acyl group of formula —C(O)—$R_5$ is a caproyl, laurolyl, myristoyl, palmitoyl, stearoyl, palmioleoyl, oleoyl, linoleoyl, or linolenoyl group.

The N-acylated amino acids can be obtained by methods well known to those skilled in the art. For example, the N-acylated amino acids can be obtained by reacting an amino acid with an acid halide of formula T-C(O)—$R_5$, wherein T is a halide, preferably chloride, and $R_1$ is as defined above, using methods well known to those skilled in the art. When N-acylating the amino acid with the acid halide of formula T-C(O)—$R_5$, it may be necessary to protect some other functional group of the amino acid or the acid halide with a protecting group that is subsequently removed after the acylation reaction. One of ordinary skill in the art would readily know what functional groups would need to be protected before acylating the amino acid with the acid halide of formula T-C(O)—$R_5$. Suitable protecting groups are known to those skilled in the art such as those described in T. W. Greene, et al. *Protective Groups in Organic Synthesis*, 3$^{rd}$ ed. (1999).

Acid halides can be obtained using methods well known to those skilled in the art such as those described in J. March, *Advanced Organic Chemistry, Reaction Mechanisms and Structure*, 4$^{th}$ ed. John Wiley & Sons, NY, 1992, pp. 437-8. For example, acid halides can be prepared by reacting a carboxylic acid with thionyl chloride, bromide, or iodide. Acid chlorides and bromides can also be prepared by reacting a carboxylic acid with phosphorous trichloride or phosphorous tribromide, respectively. Acid chlorides can also be prepared by reacting a carboxylic acid with $Ph_3P$ in carbon tetrachloride. Acid fluorides can be prepared by reacting a carboxylic acid with cyanuric fluoride.

8.5 The Pharmaceutically Acceptable Solvent

Any pharmaceutically acceptable organic solvent can be used in the pharmaceutical compositions of the invention. Representative, pharmaceutically acceptable organic solvents include, but are not limited to, pyrrolidone, N-methyl-2-pyrrolidone, polyethylene glycol, propylene glycol (i.e., 1,3-propylene glycol), glycerol formal, isosorbid dimethyl ether, ethanol, dimethyl sulfoxide, tetraglycol, tetrahydrofurfuryl alcohol, triacetin, propylene carbonate, dimethyl acetamide, dimethyl formamide, dimethyl sulfoxide, and combinations thereof.

In one embodiment, the pharmaceutically acceptable organic solvent is a water soluble solvent. A representative pharmaceutically acceptable water soluble organic solvents is triacetin.

In one embodiment, the pharmaceutically acceptable organic solvent is a water miscible solvent. Representative pharmaceutically acceptable water miscible organic solvents include, but are not limited to, glycerol formal, polyethylene glycol, and propylene glycol.

In one embodiment, the pharmaceutically acceptable organic solvent comprises pyrrolidone. In one embodiment, the pharmaceutically acceptable organic solvent is pyrrolidone substantially free of another organic solvent.

In one embodiment, the pharmaceutically acceptable organic solvent comprises N-methyl-2-pyrrolidone. In one embodiment, the pharmaceutically acceptable organic solvent is N-methyl-2-pyrrolidone substantially free of another organic solvent.

In one embodiment, the pharmaceutically acceptable organic solvent comprises polyethylene glycol. In one embodiment, the pharmaceutically acceptable organic solvent is polyethylene glycol substantially free of another organic solvent.

In one embodiment, the pharmaceutically acceptable organic solvent comprises propylene glycol. In one embodiment, the pharmaceutically acceptable organic solvent is propylene glycol substantially free of another organic solvent.

In one embodiment, the pharmaceutically acceptable organic solvent comprises glycerol formal. In one embodiment, the pharmaceutically acceptable organic solvent is glycerol formal substantially free of another organic solvent.

In one embodiment, the pharmaceutically acceptable organic solvent comprises isosorbid dimethyl ether. In one embodiment, the pharmaceutically acceptable organic solvent is isosorbid dimethyl ether substantially free of another organic solvent.

In one embodiment, the pharmaceutically acceptable organic solvent comprises ethanol. In one embodiment, the pharmaceutically acceptable organic solvent is ethanol substantially free of another organic solvent.

In one embodiment, the pharmaceutically acceptable organic solvent comprises dimethyl sulfoxide. In one embodiment, the pharmaceutically acceptable organic solvent is dimethyl sulfoxide substantially free of another organic solvent.

In one embodiment, the pharmaceutically acceptable organic solvent comprises tetraglycol. In one embodiment, the pharmaceutically acceptable organic solvent is tetraglycol substantially free of another organic solvent.

In one embodiment, the pharmaceutically acceptable organic solvent comprises tetrahydrofurfuryl alcohol. In one embodiment, the pharmaceutically acceptable organic solvent is tetrahydrofurfuryl alcohol substantially free of another organic solvent.

In one embodiment, the pharmaceutically acceptable organic solvent comprises triacetin. In one embodiment, the pharmaceutically acceptable organic solvent is triacetin substantially free of another organic solvent.

In one embodiment, the pharmaceutically acceptable organic solvent comprises propylene carbonate. In one embodiment, the pharmaceutically acceptable organic solvent is propylene carbonate substantially free of another organic solvent.

In one embodiment, the pharmaceutically acceptable organic solvent comprises dimethyl acetamide. In one embodiment, the pharmaceutically acceptable organic solvent is dimethyl acetamide substantially free of another organic solvent.

In one embodiment, the pharmaceutically acceptable organic solvent comprises dimethyl formamide. In one embodiment, the pharmaceutically acceptable organic solvent is dimethyl formamide substantially free of another organic solvent.

In one embodiment, the pharmaceutically acceptable organic solvent is propylene glycol in glycerol formal substantially free of another organic solvent.

In one embodiment, the pharmaceutically acceptable organic solvent is about 10 percent propylene glycol in glycerol formal.

In one embodiment, the pharmaceutically acceptable organic solvent is a solvent that is recognized as GRAS by the FDA for administration or consumption by animals.

In one embodiment, the pharmaceutically acceptable organic solvent is a solvent that is recognized as GRAS by the FDA for administration or consumption by humans.

In one embodiment, the pharmaceutically acceptable organic solvent is substantially free of water. Pharmaceutically acceptable organic solvents that are substantially free of water are advantageous since they are not conducive to bacterial growth. Accordingly, it is typically not necessary to include a preservative in pharmaceutical compositions that are substantially free of water.

8.6 The Pharmaceutically Active Compound

Examples of pharmaceutically active agents useful in the composition and methods of the invention include, but are not limited to, α-adrenergic agonists, β-adrenergic agonists, α-adrenergic blockers, β-adrenergic blockers, aldose reductase inhibitors, anabolics, analgesics (narcotic and non-narcotic), androgens, anesthetics, anorexics, anthelmintics (e.g., cestode, nematode, onchocerca, schistosoma, and the like), anti-allergics, anti-ameboics, anti-androgens, anti-anginals, anti-arrhythmics, anti-arteriosclerotics, anti-arthritics, antibiotics and other antibacterials, anti-cholinergics, anti-convulsants, anti-depressants, anti-diabetics agents, anti-diarrheals, anti-diuretics, anti-estrogens, antifungals, anti-glaucomas, anti-gonadotropins, anti-gout agents, anti-histaminics, anti-hyperlipoproteinemics, anti-hypertensives, anti-hyperthyroid agents, anti-hypertrophy agents, anti-hypotensives, anti-hypothyroid agents, anti-inflammatories, anti-malarials, antimicrobials, anti-migraine agents, anti-nausea agents, anti-neoplastics, antioxidants, antiparasitic agents, anti-parkinsonian agents, anti-pheochromocytoma agents, anti-pneumocytis agents, antiproliferative agents, anti-protozoals (e.g., leishmania, trichomonas, trypansoma, and the like), anti-pruritic agents, anti-psoratic agents, anti-psychotic agents, anti-pyretics, anti-rheumatics, anti ricketts agents, anti-seborrheic agents, antiseptics, anti-spasmodic agents, anti-thrombotic agents, antitussives, anti-ulcer agents, anti-urolithic agents, anti-venins, antivirals, anxiolytics, benzodiazepine antagonists, bronchodilators, calcium channel blockers, calcium regulators, cardiotonics, chelating agents, chemotherapeutics, cholecystokinin antagonists, cholelitholytic agents, choleretics, cholinergics, cholinesterase inhibitors, cholinesterase reactivators, central nervous system stimulants and agents, decongestants, diuretics, dopamine receptor agonists, drugs for treating or preventing pain, ectoparasiticides, enzymes, enzyme inducers, estrogens, gastric secretion inhibitors, glucocorticoids, gonad-stimulating principles, gonadotropic hormones, growth hormones, growth hormone releasing factors, growth stimulants, hemolytics, heparin agonists, hepatoprotectants, hypnotics, immune system boosters, immunomodulators, immunosuppressants, lactation stimulating hormones, LH-RH stimulating agonists, lipotropics, lupus erythmatosus suppressants, mineral corticoids, miotics, monoamine oxidase inhibitors, mucolytics, muscle relaxants, narcotic antagonists, neuroprotectives, neotropics, ovarian hormones, oxytocics, pepsin inhibitors, peristaltic stimulators, progestrogens, prolactin inhibitors, protoglandins, prostaglandin analogs, protease inhibitors, respiratory stimulants, sclerosing agents, sedatives, steroids, thrombolytics, thyrotropic hormones, transdermal penetration enhancers, uricosurics, vasoconstrictors, vasodilators (e.g., cerebral, coronary, peopheral, and the like), vasoprotectants, vitamins, vitamin source extracts, vulneraries (including, but not limited to, those listed in U.S. Pat. No. 5,719,197, the entire disclosure of which is incorporated herein by reference), and combinations thereof. Other additionally or alternately acceptable pharmaceutically active agents can be found, e.g., in U.S. Pat. No. 6,221,383, the entire disclosure of which is incorporated herein by reference.

In one embodiment, the pharmaceutically active compound is an antibacterial agent. Examples of useful antibacterial agents include, but are not limited to, β-lactam antibiotics such as penicillins, amoxicillin, ampicillin, and cephalosporins; macrolide antibiotics such as oleandomycin and erythromycin; tetracyclines such as tetracycline, oxytetracycline, and chlortetracycline; procaine penicillin G; quinolones such as nalidixic acid and norfloxacin; sulfonamides; chloramphenicol; florfenicol; thiamphenicol, aminoglycosides such as streptomycin, kanamycin, and gentamycins; nucleoside antibiotics such as polyoxin B; actinorhodine; bacitracin; candicidin A; ceftiofor; clindamycin; cycloheximide; cycloserine; fosfomycin; griseofulvin; metronidazole; monensin; novobiocin; rifampin; streptothricin; tetranactin; tilmicosin; tylosin; actinomycin D; adriamycin; bleomycin B2; glycolipids such as moenomycin A; mitomycin C; nojirimycin; valinomycin; and vancomycin; (See, e.g., Bradford P. Smith, *Large Animal Internal Medicine,* 2nd edn., Mosby, St. Louis, 1996, p. 644, and S. Birchard and R. Sherding, *Saunders Manual of Small Animal Practice*, W.B. Saunders Company, Philadelphia, 1994, p. 739).

In one embodiment, the pharmaceutically active compound is an antifungal agent. Examples of useful antifungal agents include, but are not limited to terbinafine, amphotericin B, ketaconazole, miconazole, 5-fluorocytosine, enilconazole, itraconazole, thiabendazole, and iodides (See, e.g., Bradford P. Smith, *Large Animal Internal Medicine,* 2nd edn., Mosby, St. Louis, 1996, p. 576, and S. Birchard and R. Sherding, *Saunders Manual of Small Animal Practice*, W.B. Saunders Company, Philadelphia, 1994, p. 576).

In one embodiment, the pharmaceutically active compound is an antiviral agent. Examples of useful antiviral agents include, but are not limited to, interferon and adefovir (See, e.g., Bradford P. Smith, *Large Animal Internal Medicine,* 2nd edn., Mosby, St. Louis, 1996, p. 646).

In one embodiment, the pharmaceutically active compound is an antiparasitic agent. Examples of useful antiparasitic agents include, but are not limited to, benzimidazoles, such as thiabendazole, fenbendazole, mebendazole, oxfendazole, oxibendazole, albendazole, parbendazole, and febantel; tetrahydropyridines such as morantel tartrate/pyrantel pamoate; levamisole, organophosphates such as haloxon, coumaphos, trichlorfon, and dichlorvos; piperazine salts; ivermectin; and phenothiazine (See, e.g., Bradford P. Smith, *Large Animal Internal Medicine,* 2nd edn., Mosby, St. Louis, 1996, p. 1688).

In one embodiment, the pharmaceutically active compound is an anti-inflammatory agent. Examples of useful antiinflammatory agents include, but are not limited to, steroids such as betamethazone; corticosteroids such as dexamethasone; antihistamines; and non-steroidal antiinflammatory drugs such as aspirin, flunixin meglumine, phenylbutazone, diclofenac, naproxen, ketoprofen, carprofen, and ibuprofin (See, e.g., Bradford P. Smith, *Large Animal Internal Medicine,* 2nd edn., Mosby, St. Louis, 1996, p. 645).

In one embodiment, the pharmaceutically active compound is a protein.

In one embodiment, the pharmaceutically active compound is a hormone.

In one embodiment, the pharmaceutically active compound is a peptide.

In one embodiment, the pharmaceutically active compound is insulin.

In one embodiment, the pharmaceutically active compound is an anti-depressant.

In one embodiment, the pharmaceutically active compound is fluoxetine.

One of ordinary skill in the art will readily recognize what pharmaceutically active compounds are neutral pharmaceutically active compounds and what pharmaceutically active compounds can form salts.

8.7 The Pharmaceutical Compositions

8.7.1 Pharmaceutical Compositions Comprising (i) an Amino Acid Ester or Amino Acid Amide and (ii) an Acidic Pharmaceutically Active Compound The amino acid ester can be any amino acid ester described above.

The amino acid amide can be any amino acid amide described above.

The acidic pharmaceutically active compound can be any acidic pharmaceutically active compound.

In one embodiment, the acidic pharmaceutically active compound is an antiinflammatory selected from aspirin, flunixin, diclofenac, naproxen, ketoprofen, carprofen, and ibuprofen.

In one embodiment, the pharmaceutically active compound is a phosphorylated nucleotide such as adefovir.

In one embodiment, the pharmaceutical composition is a solid. Without wishing to be bound by theory, it is believed that the solid is a salt formed between the amino acid ester or amino acid amide and the acidic pharmaceutically active compound wherein the acidic pharmaceutically active compound protonates the α-amino group of the amino acid ester or amino acid amide.

In one embodiment, the pharmaceutical composition further comprises a pharmaceutically acceptable organic solvent.

The pharmaceutically acceptable organic solvent can be any pharmaceutically acceptable organic solvent described above.

In one embodiment, the pharmaceutical composition further comprising a solvent is a suspension of solid particles in the pharmaceutically acceptable organic solvent. Without wishing to be bound by theory, it is believed that the solid particles comprise a salt formed between the amino acid ester or amino acid amide and the acidic pharmaceutically active compound wherein the acidic pharmaceutically active compound protonates the α-amino group of the amino acid ester or amino acid amide.

In one embodiment, comprising a pharmaceutically acceptable organic solvent the pharmaceutical composition is injectable and forms a precipitate when injected into water.

When the injectable pharmaceutical compositions are injected into water they form a precipitate. Without wishing to be bound by theory, it is believed that the α-amino group of the amino acid ester or amino acid amide is protonated by the acidic pharmaceutically active compound to form a salt that is soluble in the pharmaceutically acceptable organic solvent but insoluble in water. Accordingly, when the pharmaceutical compositions are injected into an animal, at least a portion of the pharmaceutical composition precipitates at the injection site to provide a drug depot. Without wishing to be bound by theory, it is believed that when the pharmaceutically compositions are injected into an animal, the pharmaceutically acceptable organic solvent diffuses away from the injection site and aqueous bodily fluids diffuse towards the injection site, resulting in an increase in concentration of water at the injection site, that causes at least a portion of the composition to precipitate and form a drug depot. The precipitate can take the form of a solid, a crystal, a gummy mass, or a gel. The precipitate, however, provides a depot of the pharmaceutically active compound at the injection site that releases the pharmaceutically active compound over time. Pharmaceutical compositions that are suspensions can also form drug depots when injected into an animal.

The molar ratio of acidic groups on the acidic pharmaceutically active compound to the amino acid ester or amino acid amide is typically about 1.5:1, preferably about 1.25:1, more preferably about 1.1:1. and most preferably about 1:1. Accordingly, when the acidic pharmaceutically active compound is a mono-protic carboxylic acid the molar ratio of the acidic pharmaceutically active compound to the amino acid ester or amino acid amide is about 1.5:1, preferably about 1.25:1, more preferably about 1.1:1, and most preferably about 1:1. When the acidic pharmaceutically active compound is a dicarboxylic acid, however, the ratio of the acidic pharmaceutically active compound to the amino acid ester or amino acid amide is typically about 0.75:1, preferably about 0.625:1, more preferably about 0.55:1, and most preferably about 0.5:1.

When the molar ratio of acidic groups on the acidic pharmaceutically active compound to the amino acid ester or amino acid amide is greater than 1, the pharmaceutical composition will also include the non-salt or free form of the acidic pharmaceutically active compound. Compositions further comprising the free form of the acidic pharmaceutically active compound provide an initial dose or "burst" of the acidic pharmaceutically active compound when administered to an animal. Accordingly, in some embodiments, the molar ratio of acidic groups on the acidic pharmaceutically active compound to the amino acid ester or amino acid amide is greater than 1 to provide a burst.

Typically, however, the pharmaceutical composition includes about 1 equivalent of amino acid ester or amino acid amide for each equivalent of acidic functional groups in the acidic pharmaceutically active compound so that there is substantially no free acidic pharmaceutically active compound. For example, if the acidic pharmaceutically active compound has a single acidic functional group, the acidic pharmaceutical composition includes about 1 equivalent of amino acid ester or amino acid amide for each equivalent of acidic pharmaceutically active compound. If the acidic pharmaceutically active compound, however, has two acidic functional group, the acidic pharmaceutical composition typically includes about 2 equivalent of amino acid ester or amino acid amide for each equivalent of acidic pharmaceutically active compound.

By varying the lipophilicity and/or molecular weight of the amino acid ester or amino acid amide it is possible to vary the rate at which the acidic pharmaceutically active compound is released from the drug depot. Generally, the more lipophilic the amino acid ester or amino acid amide, the more slowly drug is released. The lipophilicity and/or molecular weight of the amino acid ester or amino acid amide can be varied by varying the amino acid and/or the alcohol (or amine) used to form the amino acid ester (or amino acid amide). For example, the lipophilicity and/or molecular weight of the amino acid ester can be varied by varying the $R_1$ hydrocarbon group of the amino acid ester. Typically, increasing the length of $R_1$ increase the lipophilicity of the amino acid ester. Similarly, the lipophilicity and/or molecular weight of the amino acid amide can be varied by varying the $R_3$ or $R_4$ group of the amino acid amide.

The combined amount of the acidic pharmaceutically active compound and amino acid ester or amino acid amide typically ranges from about 1 to 90 percent by weight of the pharmaceutical composition, preferably about 5 to 80 percent by weight of the pharmaceutical composition, more preferably about 7.5 to 70 percent by weight of the pharmaceutical composition, and most preferably about 10 to 60 by weight of the pharmaceutical composition.

In one embodiment, the pharmaceutically active compound is flunixin.

In one embodiment, the pharmaceutically active compound is flunixin and the amino acid ester is tryptophan octanoate.

In one embodiment, the pharmaceutically active compound is flunixin, the amino acid ester is tryptophan octanoate, and the pharmaceutically acceptable organic solvent is about 5% propylene glycol in glycerol formal.

In one embodiment, the pharmaceutically active compound is flunixin, the amino acid ester is tryptophan octanoate, the pharmaceutically acceptable organic solvent is about 5% propylene glycol in glycerol formal, and the combined amount of flunixin and the tryptophan octanoate ranges from about 25 to 40 percent by weight of the composition.

In one embodiment, the pharmaceutically active compound is flunixin, the amino acid ester is tryptophan octanoate, the pharmaceutically acceptable organic solvent is about 5% propylene glycol in glycerol formal, and the combined amount of flunixin and the tryptophan octanoate ranges from about 30 to 35 percent by weight of the composition.

In one embodiment, the pharmaceutically active compound is flunixin and the amino acid ester is tryptophan butanoate.

In one embodiment, the pharmaceutically active compound is flunixin, the amino acid ester is tryptophan butanoate, and the pharmaceutically acceptable organic solvent is about 5% propylene glycol in glycerol formal.

In one embodiment, the pharmaceutically active compound is flunixin, the amino acid ester is tryptophan butanoate, the pharmaceutically acceptable organic solvent is about 5% propylene glycol in glycerol formal, and the combined amount of flunixin and the tryptophan butanoate ranges from about 20 to 35 percent by weight of the composition.

In one embodiment, the pharmaceutically active compound is flunixin, the amino acid ester is tryptophan butanoate, the pharmaceutically acceptable organic solvent is about 5% propylene glycol in glycerol formal, and the combined amount of flunixin and the tryptophan butanoate ranges from about 25 to 32 percent by weight of the composition.

In one embodiment, the amino acid ester or amide is an amino acid ester or amide of lysine. Without wishing to be bound by theory it is believed that the amino acid ester or amide of lysine cross-links two molecules of acidic pharmaceutically active compound as depicted below for an ester of lysine:

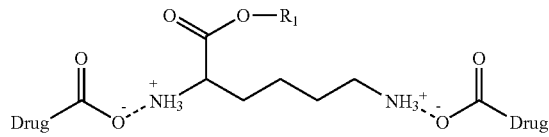

wherein $R_1$ has the meaning described above and Drug-C(O)O$^-$ is the acidic pharmaceutically active compound.

In one embodiment, the acidic pharmaceutically active compound is a phosphorylated nucleotide such as adefovir.

The molar ratio of acidic groups on the pharmaceutically active compound to amine groups on the amino acid ester or amide of lysine typically ranges from about 1.5:1 to 1:1.5. In one embodiment, the molar ratio of acidic groups on the pharmaceutically active compound to amine groups on the amino acid ester or amide of lysine ranges from about 1.25:1 to 1:1.25. In one embodiment, the molar ratio of acidic groups on the pharmaceutically active compound to amine groups on the amino acid ester or amide of lysine ranges from about 1.1:1 to 1:1.1. In one embodiment, the molar ratio of acidic groups on the pharmaceutically active compound to amine groups on the amino acid ester or amide of lysine is about 1:1.

In one embodiment, the molar ratio of amine groups on the amino acid ester or amide of lysine relative to acidic groups on the pharmaceutically active compound is greater than about 1:1. In one embodiment, the molar ratio of amine groups on the amino acid ester or amide of lysine relative to acidic groups on the pharmaceutically active compound is greater than about 2:1. In one embodiment, the molar ratio of amine groups on the amino acid ester or amide of lysine relative to acidic groups on the pharmaceutically active compound is greater than about 5:1. In one embodiment, the molar ratio of amine groups on the amino acid ester or amide of lysine relative to acidic groups on the pharmaceutically active compound is greater than about 8:1. In one embodiment, the molar ratio of amine groups on the amino acid ester or amide of lysine relative to acidic groups on the pharmaceutically active compound is greater than about 10:1. In one embodiment, the molar ratio of amine groups on the amino acid ester or amide of lysine relative to acidic groups on the pharmaceutically active compound is greater than about 12:1. In one embodiment, the molar ratio of amine groups on the amino acid ester or amide of lysine relative to acidic groups on the pharmaceutically active compound ranges from about 2:1 to 5:1. In one embodiment, the molar ratio of amine groups on the amino acid ester or amide of lysine relative to acidic groups on the pharmaceutically active compound ranges from about 2:1 to 8:1. In one embodiment, the molar ratio of amine groups on the amino acid ester or amide of lysine relative to acidic groups on the pharmaceutically active compound ranges from about 2:1 to 10:1. In one embodiment, the molar ratio of amine groups on the amino acid ester or amide of lysine relative to acidic groups on the pharmaceutically active compound ranges from about 2:1 to 12:1.

In one embodiment, the molar ratio of amine groups on the amino acid ester or amide of lysine relative to acidic groups on the pharmaceutically active compound is greater than about 1:1 and some or all of the excess amino groups on the amino acid ester or amide of lysine are neutralized with a fatty acid. Any of the fatty acids described above can be used to neutralize the excess amino groups on the amino acid ester or amide of lysine.

8.7.2 Pharmaceutical Compositions Comprising (i) an Amino Acid Ester or Amino Acid Amide, (ii) a Carboxylic Acid, (iii) a Pharmaceutically Active Compound or a Pharmaceutically Acceptable Salt Thereof The amino acid ester can be any amino acid ester described above.

The amino acid amide can be any amino acid amide described above.

The carboxylic acid can be any carboxylic acid described above.

In one embodiment, the carboxylic acid is a fatty acid.

In one embodiment, the carboxylic acid is an N-acylated amino acid.

In one embodiment, the pharmaceutical composition is a solid. Without wishing to be bound by theory, it is believed that the solid comprises a salt formed between the amino acid ester or amino acid amide and the carboxylic acid wherein the carboxylic acidic protonates the α-amino group of the amino acid ester or amino acid amide.

In one embodiment, the pharmaceutical composition further comprises a pharmaceutically acceptable organic solvent.

The pharmaceutically acceptable organic solvent can be any pharmaceutically acceptable organic solvent described above.

In one embodiment, the pharmaceutical composition further comprising a pharmaceutically acceptable organic solvent is a suspension of solid particles in the pharmaceutically acceptable organic solvent. Without wishing to be bound by theory, it is believed that the solid particles are a salt formed between the amino acid ester or amino acid amide and the carboxylic acid wherein the carboxylic acid protonates the α-amino group of the amino acid ester or amino acid amide.

In one embodiment, comprising a pharmaceutically acceptable organic solvent, the pharmaceutical composition is injectable and forms a precipitate when injected into water.

The pharmaceutically active compound can be a neutral pharmaceutically active compound or a pharmaceutically acceptable salt of a basic or acidic pharmaceutically active compound.

In one embodiment, the pharmaceutically active compound is a neutral pharmaceutically active compound. When the pharmaceutically active compound is a neutral pharmaceutically active compound, the pharmaceutical composition includes about 1 equivalent of amino acid ester or amino acid amide for each equivalent of acidic groups in the carboxylic acid. For example, if the carboxylic acid is a mono-protic carboxylic acid, the pharmaceutical composition includes about 1 equivalent of amino acid ester or amino acid amide for each equivalent of carboxylic acid and if the carboxylic acid is a di-carboxylic acid, the pharmaceutical composition includes about 2 equivalent of amino acid ester or amino acid amide for each equivalent of carboxylic acid.

In one embodiment, the pharmaceutically active compound is a neutral pharmaceutically active compound and the carboxylic acid is a fatty acid.

In one embodiment, the pharmaceutically active compound is a neutral pharmaceutically active compound and the carboxylic acid is an N-acylated amino acid.

The amount of neutral pharmaceutically active compound in the pharmaceutical composition typically ranges from about 1 to 90 percent by weight of the pharmaceutical composition, preferably about 5 to 80 percent by weight of the pharmaceutical composition, more preferably about 7.5 to 70 percent by weight of the pharmaceutical composition, and most preferably about 10 to 60 by weight of the pharmaceutical composition.

One of ordinary skill in the art will recognize, however, that the amount of neutral pharmaceutically active compound in the pharmaceutical composition can vary widely depending on the neutral pharmaceutically active compound, the solvent, the amino acid ester or amino acid amide, and the carboxylic acid used in the pharmaceutical composition.

The combined amount of the amino acid ester or amino acid amide and the carboxylic acid in the pharmaceutical compositions that further comprise a pharmaceutically acceptable organic solvent typically ranges from about 2 percent to 50 percent by weight of the pharmaceutical composition, preferably about 3 percent to 35 percent by weight of the pharmaceutical composition, more preferably about 4 percent to 25 percent by weight of the pharmaceutical composition, even more preferably about 5 percent to 20 percent by weight of the pharmaceutical composition, and most preferably about 5 percent to 15 percent by weight of the pharmaceutical composition.

In one embodiment, the pharmaceutically active compound is insulin, the carboxylic acid is decanoic acid, the amino acid ester is tyrosine decanoate, the solvent is glycerol formal, the molar ratio of decanoic acid to tyrosine decanoate is about 1:1, the insulin is present in an amount ranging from about 0.5 to 15 percent by weight of the pharmaceutical composition, and the combined amount of decanoic acid and tyrosine decanoate ranges from about 15 to 25 percent by weight of the pharmaceutical composition.

In one embodiment, the pharmaceutically active compound is fluoxetine, the carboxylic acid is lauric acid, the amino acid ester tyrosine butanoate, the solvent is 10 percent propylene glycol in glycerol formal, the amount of fluoxetine ranges from about 5 to 30 percent by weight of the composition, and the molar ratio of fluoxetine:lauric acid:tryptophan butanoate is about 1:2:1. Pharmaceutical compositions of the invention containing fluoxetine can be administered to dogs to treat separation anxiety and to cats to treat spraying.

In one embodiment, the pharmaceutically active compound is a pharmaceutically acceptable salt of an acidic or basic pharmaceutically active compound.

In one embodiment, the salt of the pharmaceutically active compound is a salt formed between a basic pharmaceutically active compound and an acid.

In one embodiment, the salt of the pharmaceutically active compound is a salt formed between a basic pharmaceutically active compound and a carboxylic acid.

In one embodiment, the salt of the pharmaceutically active compound is a salt formed between a basic pharmaceutically active compound and a fatty acid.

In one embodiment, the salt of the pharmaceutically active compound is a salt formed between a basic pharmaceutically active compound and an N-acylated amino acid.

In one embodiment, the salt of the pharmaceutically active compound is a salt formed between an acidic pharmaceutically active compound and a base.

In one embodiment, the salt of the pharmaceutically active compound is a salt formed between an acidic pharmaceutically active compound and an amino acid ester or amino acid amide.

In one embodiment, the carboxylic acid is a fatty acid and the pharmaceutically active compound is a pharmaceutically acceptable salt of an acidic or basic pharmaceutically active compound.

In one embodiment, the carboxylic acid is a fatty acid and the salt of the pharmaceutically active compound is a salt formed between a basic pharmaceutically active compound and an acid.

In one embodiment, the carboxylic acid is a fatty acid and the salt of the pharmaceutically active compound is a salt formed between a basic pharmaceutically active compound and a carboxylic acid.

In one embodiment, the carboxylic acid is a fatty acid and the salt of the pharmaceutically active compound is a salt formed between a basic pharmaceutically active compound and a fatty acid.

In one embodiment, the carboxylic acid is a fatty acid and the salt of the pharmaceutically active compound is a salt formed between a basic pharmaceutically active compound and an N-acylated amino acid.

In one embodiment, the carboxylic acid is a fatty acid and the salt of the pharmaceutically active compound is a salt formed between an acidic pharmaceutically active compound and a base.

In one embodiment, the carboxylic acid is a fatty acid and the salt of the pharmaceutically active compound is a salt formed between an acidic pharmaceutically active compound and an amino acid ester or amino acid amide.

In one embodiment, the carboxylic acid is an N-acylated amino acid and the pharmaceutically active compound is a pharmaceutically acceptable salt of an acidic or basic pharmaceutically active compound.

In one embodiment, the carboxylic acid is an N-acylated amino acid and the salt of the pharmaceutically active compound is a salt formed between a basic pharmaceutically active compound and an acid.

In one embodiment, the carboxylic acid is an N-acylated amino acid and the salt of the pharmaceutically active compound is a salt formed between a basic pharmaceutically active compound and a carboxylic acid.

In one embodiment, the carboxylic acid is an N-acylated amino acid and the salt of the pharmaceutically active compound is a salt formed between a basic pharmaceutically active compound and a fatty acid.

In one embodiment, the carboxylic acid is an N-acylated amino acid and the salt of the pharmaceutically active compound is a salt formed between a basic pharmaceutically active compound and an N-acylated amino acid.

In one embodiment, the carboxylic acid is an N-acylated amino acid and the salt of the pharmaceutically active compound is a salt formed between an acidic pharmaceutically active compound and a base.

In one embodiment, the carboxylic acid is an N-acylated amino acid and the salt of the pharmaceutically active compound is a salt formed between an acidic pharmaceutically active compound and a amino acid ester or amino acid amide.

When the pharmaceutically active compound is a salt of a pharmaceutically active compound, the pharmaceutical composition includes about 1 equivalent of amino acid ester or amino acid amide for each equivalent of acidic groups in the carboxylic acid.

The combined concentration of the amino acid ester or amino acid amide and the carboxylic acid in the pharmaceutical compositions typically ranges from about 2 percent to 50 percent by weight of the pharmaceutical composition, preferably about 3 percent to 35 percent by weight of the pharmaceutical composition, more preferably about 4 percent to 25 percent by weight of the pharmaceutical composition, even more preferably about 5 percent to 20 percent by weight of the pharmaceutical composition, and most preferably about 5 percent to 15 percent by weight of the pharmaceutical composition.

The amount of the salt of the acidic or basic pharmaceutically active compound in the pharmaceutical compositions typically ranges from about 1 to 90 percent by weight of the pharmaceutical composition, preferably about 5 to 80 percent by weight of the pharmaceutical composition, more preferably about 7.5 to 70 percent by weight of the pharmaceutical composition, and most preferably about 10 to 60 by weight of the pharmaceutical composition.

One of ordinary skill in the art will recognize, however, that the amount of the salt of the acidic or basic pharmaceutically active compound in the pharmaceutical composition can vary widely depending on the pharmaceutically active compound, the solvent, the amino acid ester or amino acid amide, and the carboxylic acid used in the pharmaceutical composition.

The pharmaceutically acceptable organic solvent can be any pharmaceutically acceptable organic solvent described above.

Again, without wishing to be bound by theory, it is believed that when the pharmaceutical compositions further comprising a pharmaceutically acceptable organic solvent are injected into an animal, the pharmaceutically acceptable organic solvent diffuses away from the injection site and aqueous bodily fluids diffuse towards the injection site, resulting in an increase in concentration of water at the injection site, that causes at least a portion of the composition to precipitate and form a drug depot. Again, when the pharmaceutical composition is injected into an animal, the salt of the amino acid ester or amino acid amide and the carboxylic acid precipitates to form a drug depot that slowly releases the pharmaceutically active compound. The salt of the pharmaceutically active compound, however, may also form a precipitate.

In a preferred embodiment, the pharmaceutical composition comprises the amino acid ester or amino acid amide, a fatty acid, a salt of a pharmaceutically active compound, and a pharmaceutically acceptable organic solvent, wherein the salt of the pharmaceutically active compound is a salt formed between an acidic pharmaceutically active compound and an amino acid ester or amino acid amide. In this embodiment, a salt formed between the amino acid ester or amino acid amide and the fatty acid precipitates and a salt formed between the acidic pharmaceutically active compound and the amino acid ester or amino acid amide precipitates when the pharmaceutical composition is injected into an animal to form a drug depot that slowly releases the pharmaceutically active compound over time.

In another preferred embodiment, the pharmaceutical composition comprises the amino acid ester or amino acid amide, a N-acylated amino acid, a salt of a pharmaceutically active compound, and a pharmaceutically acceptable organic solvent, wherein the salt of the pharmaceutically active compound is a salt formed between an acidic pharmaceutically active compound and an amino acid ester or amino acid amide. In this embodiment, a salt formed between the amino acid ester or amino acid amide and the N-acylated amino acid precipitates and a salt formed between the acidic pharmaceutically active compound and the amino acid ester or amino acid amide precipitates when the pharmaceutical composition is injected into an animal to form a drug depot that slowly releases the pharmaceutically active compound over time.

When the compositions include an amino acid ester or amino acid amide, a carboxylic acid, and a salt of a pharmaceutically active compound, it is recognized that there will be an exchange of the anions (and cations) that form the salt of the pharmaceutically active compound with the anions (and cations) that form the salt between the carboxylic acid and the amino acid ester or amino acid amide. For example, if the salt of a pharmaceutically active compound is a salt formed between a basic pharmaceutically active compound and a fatty acid and the carboxylic acid is a N-acylated amino acid, the pharmaceutical composition will include each of the following species: a salt between the basic pharmaceutically active compound and the fatty acid, a salt between the basic pharmaceutically active compound and the N-acylated amino acid, a salt between the amino acid ester or amino acid amide and the fatty acid, and a salt between the amino acid ester or amino acid amide and the N-acylated amino acid. Any one or all of these species can precipitate when the pharmaceutical composition is injected into an animal to form a drug depot that slowly releases the pharmaceutically active compound over time.

By varying the lipophilicity and/or molecular weight of the amino acid ester or amino acid amide it is possible to vary the rate at which the acidic pharmaceutically active compound is released from the drug depot. Generally, the more lipophilic the amino acid ester or amino acid amide, the more slowly drug is released. The lipophilicity and/or molecular weight of the amino acid ester or amino acid amide can be varied by varying the amino acid and/or the alcohol (or amine) used to form the amino acid ester (or amino acid amide). For example, the lipophilicity and/or molecular weight of the amino acid ester can be varied by varying the $R_1$ hydrocarbon group of the amino acid ester. Typically, increasing the length of $R_1$ increase the lipophilicity of the amino acid ester. Similarly, the lipophilicity and/or molecular weight of the amino acid amide can be varied by varying the $R_3$ or $R_4$ group of the amino acid amide. The rate at which the pharmaceutically active compound is released from the drug depot can also be varied by varying the lipophilicity and/or molecular weight of the carboxylic acid. Generally, the more lipophilic the carboxylic acid, the more slowly drug is released. The lipophilicity and/or molecular weight of the carboxylic acid can be varied by varying the molecular weight of the carboxylic acid. Generally, the higher the molecular weight of the carboxylic acid, the more slowly drug is released. Similarly, the lipophilicity and/or molecular weight of the N-acyl amino acid can be varied by varying the $R_5$ group of the N-acyl amino acid.

8.7.3 Pharmaceutical Compositions Comprising (i) an N-Acyl Amino Acid, and (ii) a Basic Pharmaceutically Active Compound The N-acyl amino acid can be any N-acyl amino acid described above.

The basic pharmaceutically active compound can be any basic pharmaceutically active compound.

In one embodiment, the basic pharmaceutically active compound is an antibiotic selected from the group consisting of penicillin, streptomycin, azithromycin, roxythromycin, tilmicosin, oxytetracycline, and doxycyline.

In one embodiment, the pharmaceutical composition is a solid. Without wishing to be bound by theory, it is believed that the solid is a salt formed between the N-acyl amino acid and the basic pharmaceutically active compound wherein the N-acyl amino acid protonates the basic pharmaceutically active compound.

In one embodiment, the pharmaceutical composition further comprises a pharmaceutically acceptable organic solvent.

The pharmaceutically acceptable organic solvent can be any pharmaceutically acceptable organic solvent described above.

In one embodiment, the pharmaceutical composition further comprising a solvent is a suspension of solid particles in the pharmaceutically acceptable organic solvent. Without wishing to be bound by theory, it is believed that the solid particles are a salt formed between the N-acyl amino acid and the basic pharmaceutically active compound wherein the N-acyl amino acid protonates the basic pharmaceutically active compound.

In one embodiment, comprising a pharmaceutically acceptable organic solvent the pharmaceutical composition is injectable and forms a precipitate when injected into water.

When the injectable pharmaceutical compositions further comprising a solvent are injected into water they typically form a precipitate. Without wishing to be bound by theory, it is believed that the carboxylic acid group of the N-acyl amino acid protonates the basic pharmaceutically active compound to form a salt that is soluble in the pharmaceutically acceptable organic solvent but insoluble in water. Accordingly, when the pharmaceutical compositions are injected into an animal, at least a portion of the pharmaceutical composition precipitates at the injection site to provide a drug depot. Without wishing to be bound by theory, it is believed that when the pharmaceutically compositions are injected into an animal, the pharmaceutically acceptable organic solvent diffuses away from the injection site and aqueous bodily fluids diffuse towards the injection site, resulting in an increase in concentration of water at the injection site, that causes at least a portion of the composition to precipitate and form a drug depot. The precipitate can take the form of a solid, a crystal, a gummy mass, or a gel. The precipitate, however, provides a depot of the pharmaceutically active compound at the injection site that releases the pharmaceutically active compound over time. Pharmaceutical compositions that are suspensions can also form a drug depot when injected into an animal.

The molar ratio of basic groups on the basic pharmaceutically active compound to the N-acyl amino acid is typically about 1.5:1, preferably about 1.25:1, more preferably about 1.1:1. and most preferably about 1:1. Accordingly, when the basic pharmaceutically active compound is a mono-basic compound the molar ratio of the basic pharmaceutically active compound to the N-acyl amino acid is about 1.5:1, preferably about 1.25:1, more preferably about 1.1:1, and most preferably about 1:1. When the basic pharmaceutically active compound is a dibasic compound, however, the ratio of the basic pharmaceutically active compound to the N-acyl amino acid is typically about 0.75:1, preferably about 0.625:1, more preferably about 0.55:1, and most preferably about 0.5:1.

When the molar ratio of basic groups on the basic pharmaceutically active compound to the N-acyl amino acid is greater than 1, the pharmaceutical composition will also include the non-salt or free form of the basic pharmaceutically active compound. Compositions further comprising the free form of the basic pharmaceutically active compound provide an initial dose or "burst" of the basic pharmaceutically active compound. Accordingly, in some embodiments, the molar ratio of basic groups on the basic pharmaceutically active compound to the N-acyl amino acid is greater than 1 to provide a burst.

Typically, however, the pharmaceutical composition includes about 1 equivalent of N-acyl amino acid for each equivalent of basic functional groups in the basic pharmaceutically active compound so that there is substantially no free basic pharmaceutically active compound. For example, if the basic pharmaceutically active compound has a single basic functional group, the basic pharmaceutical composition includes about 1 equivalent of N-acyl amino acid for each equivalent of basic pharmaceutically active compound. If the basic pharmaceutically active compound, however, has two basic functional group, the pharmaceutical composition typically includes about 2 equivalent of N-acyl amino acid for each equivalent of basic pharmaceutically active compound.

By varying the lipophilicity and/or molecular weight of the N-acyl amino acid it is possible to vary the rate at which the basic pharmaceutically active compound is released from the drug depot. Generally, the more lipophilic the N-acyl amino acid, the more slowly drug is released. The lipophilicity and/or molecular weight of the N-acyl amino acid can be varied by varying the amino acid and/or the acyl group used to form the N-acyl amino acid. For example, the lipophilicity and/or molecular weight of the N-acyl amino acid can be varied by varying the $R_5$ hydrocarbon group of the N-acyl amino acid. Typically, increasing the length of $R_5$ increase the lipophilicity of the N-acyl amino acid.

The combined amount of the basic pharmaceutically active compound and N-acyl amino acid in the pharmaceutical composition typically ranges from about 1 to 90 percent by weight of the pharmaceutical composition, preferably about 5 to 80 percent by weight of the pharmaceutical composition, more preferably about 7.5 to 70 percent by weight of the pharmaceutical composition, and most preferably about 10 to 60 by weight of the pharmaceutical composition.

In one embodiment, the basic pharmaceutically active compound is a fluoroquinolone. The fluoroquinolone can be any fluoroquinolone known to those skilled in the art. Representative fluoroquinolones useful in the compositions and methods of the invention include, but are not limited to, those described in BE 870,576, U.S. Pat. No. 4,448,962, DE 3,142,854, EP 047,005, EP 206,283, BE 887,574, EP 221,463, EP 140,116, EP 131,839, EP 154,780, EP 078,362, EP 310,849, EP 520,240, U.S. Pat. No. 4,499,091, U.S. Pat. No. 4,704,459, U.S. Pat. No. 4,795,751, U.S. Pat. No. 4,668,784, and U.S. Pat. No. 5,532,239, the contents of which are expressly incorporated herein by reference thereto.

Representative fluoroquinolones useful in the compositions and methods of the invention include, but are not limited to, ciprofloxacin (commercially available as Cipro®, enrofloxacin (commercially available as Baytril®), enoxacin (commercially available as Penetrex®, gatifloxacin (commercially available as Tequin®), gemifloxacin (commercially available as Factive®), levofloxacin (commercially available as Levaquin®), lomefloxacin (commercially available as Maxaquin®), moxifloxacin (commercially available as Avelox®), norfloxacin (commercially available as Noroxin®, ofloxacin (commercially available as Floxin®), sparfloxacin (commercially available as Zagam®), trovafloxacin (commercially available as Trovan®), difloxacin, cinofloxacin, pefloxacin, tosufloxacin, temafloxacin, flerofloxacin, amifloxacin, benofloxacin, danofloxacin, flerofloxacin, marbofloxacin, ruflocaxin, and sarafloxacin.

In one embodiment, the fluoroquinolone is ciprofloxacin.
In one embodiment, the fluoroquinolone is enrofloxacin.
In one embodiment, the fluoroquinolone is gatifloxacin.
In one embodiment, the fluoroquinolone is gemifloxacin.
In one embodiment, the fluoroquinolone is levofloxacin.
In one embodiment, the fluoroquinolone is lomefloxacin.
In one embodiment, the fluoroquinolone is moxifloxacin.
In one embodiment, the fluoroquinolone is ofloxacin.
In one embodiment, the fluoroquinolone is sparfloxacin.
In one embodiment, the fluoroquinolone is trovafloxacin.
In one embodiment, the fluoroquinolone is difloxacin.
In one embodiment, the fluoroquinolone is cinofloxacin.
In one embodiment, the fluoroquinolone is pefloxacin.
In one embodiment, the fluoroquinolone is tosufloxacin.
In one embodiment, the fluoroquinolone is temafloxacin.
In one embodiment, the fluoroquinolone is flerofloxacin.
In one embodiment, the fluoroquinolone is amifloxacin.
In one embodiment, the fluoroquinolone is benofloxacin.
In one embodiment, the fluoroquinolone is danofloxacin.
In one embodiment, the fluoroquinolone is flerofloxacin.
In one embodiment, the fluoroquinolone is marbofloxacin.
In one embodiment, the fluoroquinolone is ruflocaxin.
In one embodiment, the fluoroquinolone is sarafloxacin.

8.7.4 General Characteristics of the Pharmaceutical Compositions

Typically, when the compositions of the invention are injected into water the resulting precipitate is a gummy mass or a gel. Typically, the viscosity of the gummy mass or a gel ranges from about 10,000 cP to 150,000 cP. In one embodiment, the viscosity of the gummy mass or a gel ranges from about 50,000 cP to 150,000 cP. In one embodiment, the viscosity of the gummy mass or a gel ranges from about 65,000 centipoise (cP) to 150,000 cP. In one embodiment, the viscosity of the gummy mass or a gel ranges from about 75,000 centipoise (cP) to 150,000 cP. The viscosity of the gummy mass or gel can be determined by injecting the pharmaceutical composition into water to provide the gummy mass or gel, removing the water and pharmaceutically acceptable organic solvent by filtering through a 0.22 μm filter to collect the gummy mass or gel, and then measuring the viscosity of the gummy mass or gel. Viscosity can be measured, for example, using a Brookfield DV-E Viscometer (commercially available from Brookfield of Middleboro, Mass.). In another embodiment, the precipitate is a solid, i.e., resistant to flow. In another embodiment, the solid is a crystalline solid.

The rate of release of the pharmaceutically active compound from the drug depot can be controlled by varying the lipophilicity and/or molecular weight of the amino acid ester or amino acid amide. Typically, if the amino acid ester is more lipophilic the drug is released more slowly. The lipophilicity and/or molecular weight of the amino acid ester can be varied by varying the $R_1$ hydrocarbon group of the amino acid ester. Typically, increasing the length of $R_1$ increase the lipophilicity of the amino acid ester. Similarly, the lipophilicity and/or molecular weight of the amino acid amide can be varied by varying the $R_3$ or $R_4$ group of the amino acid amide.

The carboxylic acid used in the pharmaceutical composition also affects the rate of release of the pharmaceutically active compound from the drug depot. Similarly, when the carboxylic acid is an N-acyl amino acid, the rate of release of the pharmaceutically active compound from the drug depot can be controlled by varying the lipophilicity and/or molecular weight of the N-acyl amino acid. Again, if the carboxylic acid or N-acyl amino acid is more lipophilic the drug is released more slowly. The lipophilicity and/or molecular weight of the carboxylic acid can be varied by varying the number of carbon atoms in the carboxylic acid. The lipophilicity and/or molecular weight of the N-acyl amino acid can be varied by varying the hydrocarbon group, $R_5$, of the acyl group, $R_2$, i.e., by varying the acyl group of formula —C(O)—$R_5$.

The pharmaceutical compositions may further include one or more additional excipients or additives well known to those of ordinary skill in the art. For example, the pharmaceutical formulations may include a preservative to inhibit microbial growth. Suitable preservatives include, but are not limited to, parabens such as methyl, ethyl, and propyl parabens; chlorobutanol; sodium benzoate; myristyl-gamma-picolinium chloride; benzyl alcohol; and ethyl alcohol. Preservatives, when present, are typically present in an amount of about 5 mg to 250 mg per mL of pharmaceutical composition and preferably about 5 mg to 100 mg per mL of pharmaceutical composition.

In one embodiment, the compositions include a local anesthetic such as lidocaine to lessen pain at the site of the injection.

Solid pharmaceutical compositions may further comprise additional excipients well known to those of ordinary skill in the art, such as binders, diluents, lubricants. Examples off suitable excipients are described in *Remington's Pharmaceutical Sciences* (Alfonso Gennaro ed., 19th ed. 1995), incorporated herein by reference. Accordingly, the solid pharmaceutical compositions can be formulated as a tablet, for oral administration, using methods will known to those skilled in the art (*Remington's Pharmaceutical Sciences* (Alfonso Gennaro ed., 19th ed. 1995).

Similarly, the pharmaceutical compositions in the form of a gel can be formulated for oral administration by encapsulating the pharmaceutical composition in a capsule, such as a hard or soft gelatin capsule.

The components of the pharmaceutical composition (the amino acid ester or amino acid amide, the carboxylic acid, the organic solvent, and the pharmaceutically active compound, as well as any other optional components) are preferably biocompatible and non-toxic and, over time, are simply absorbed and/or metabolized by the body.

8.8 Manufacturing the Pharmaceutical Compositions

To prepare the pharmaceutical compositions of the invention comprising (i) an amino acid ester or amino acid amide, (ii) an acidic pharmaceutically active compound, and (iii) a pharmaceutically acceptable organic solvent, the amino acid ester or amino acid amide and the acidic pharmaceutically active compound are simply dissolved in the pharmaceutically acceptable organic solvent to provide a solution (typically about 90% of the amount of the solvent desired in the final pharmaceutical composition). Additional excipients and/or additives can then be dissolved in the solution. Additional pharmaceutically acceptable organic solvent is then added to provide the desired concentration of the amino acid ester or amino acid amide and the acidic pharmaceutically active compound in the pharmaceutical composition The solution of the amino acid ester or amino acid amide and the acidic pharmaceutically active compound, and additional excipients and/or additives can then be filtered, preferably sterile filtered, directly into bottles.

The solid pharmaceutical compositions comprising a (i) an amino acid ester or amino acid amide and (ii) an acidic pharmaceutically active compound are prepared in the same way as is used to prepare the pharmaceutical compositions of the invention comprising (i) an amino acid ester or amino acid amide, (ii) an acidic pharmaceutically active compound, and (iii) a pharmaceutically acceptable organic solvent, and the pharmaceutically acceptable organic solvent is simply removed by evaporation. In one embodiment, the pharmaceutically acceptable organic solvent is removed under reduced pressure. Alternatively, the pharmaceutical composition comprising (i) an amino acid ester or amino acid amide, (ii) an acidic pharmaceutically active compound, and (iii) a pharmaceutically acceptable organic solvent can be diluted with water to provide a solid precipitate and the solid precipitate collected by filtration and, optionally, dried. The resulting solid pharmaceutical composition can optionally be milled to provide smaller particles. Excipients can also be added to the resulting solid pharmaceutical compositions.

Similarly, to prepare the pharmaceutical compositions of the invention comprising (i) an amino acid ester or amino acid amide, (ii) a carboxylic acid, (iii) a neutral pharmaceutically active compound or a pharmaceutically acceptable salt of a pharmaceutically active compound, and (iv) a pharmaceutically acceptable organic solvent, the amino acid ester or amino acid amide, the carboxylic acid, and the neutral pharmaceutically active compound or a pharmaceutically acceptable salt of a pharmaceutically active compound are simply dissolved in the pharmaceutically acceptable organic solvent to provide a solution (typically about 90% of the amount of the solvent desired in the final pharmaceutical composition). Additional excipients and/or additives can then be dissolved in the solution. Additional pharmaceutically acceptable organic solvent is then added to provide the desired concentration of the amino acid ester or amino acid amide, the carboxylic acid, and the neutral pharmaceutically active compound or pharmaceutically acceptable salt of a pharmaceutically active compound in the pharmaceutical composition The solution of the amino acid ester or amino acid amide, the carboxylic acid, the neutral pharmaceutically active compound or pharmaceutically acceptable salt of a pharmaceutically active compound, and additional excipients and/or additives can then be filtered, preferably sterile filtered, directly into bottles.

The solid pharmaceutical compositions comprising a (i) an amino acid ester or amino acid amide, (ii) a carboxylic acid, and a (iii) a neutral pharmaceutically active compound or a pharmaceutically acceptable salt of a pharmaceutically active compound are prepared in the same way as is used to prepare the pharmaceutical compositions of the invention comprising (i) an amino acid ester or amino acid amide, (ii) a carboxylic acid, and a (iii) a neutral pharmaceutically active compound or a pharmaceutically acceptable salt of a pharmaceutically active compound and (iv) a pharmaceutically acceptable organic solvent, and the pharmaceutically acceptable organic solvent is simply removed by evaporation. In one embodiment, the pharmaceutically acceptable organic solvent is removed under reduced pressure. Alternatively, the pharmaceutical composition comprising (i) an amino acid ester or amino acid amide, (ii) a carboxylic acid, a (iii) a neutral pharmaceutically active compound or a pharmaceutically acceptable salt of a pharmaceutically active compound, and a pharmaceutically acceptable organic solvent can be diluted with water to provide a solid precipitate and the solid precipitate collected by filtration and, optionally, dried. The resulting solid pharmaceutical composition can optionally be milled to provide smaller particles. Excipients can also be added to the resulting solid pharmaceutical compositions.

Similarly, to prepare the pharmaceutical compositions of the invention comprising (i) a N-acyl amino acid, (ii) a basic pharmaceutically active compound, and (iii) a pharmaceutically acceptable organic solvent, the N-acyl amino acid and the basic pharmaceutically active compound are simply dissolved in the pharmaceutically acceptable organic solvent to provide a solution (typically about 90% of the amount of the solvent desired in the final pharmaceutical composition). Additional excipients and/or additives can then be dissolved in the solution. Additional pharmaceutically acceptable organic solvent is then added to provide the desired concentration of the N-acyl amino acid and the basic pharmaceutically active compound in the pharmaceutical composition The solution of the N-acyl amino acid ester and the basic pharmaceutically active compound, and additional excipients and/or additives can then be filtered, preferably sterile filtered, directly into bottles.

The solid pharmaceutical compositions comprising a (i) a N-acyl amino acid and (ii) a basic pharmaceutically active compound are prepared in the same way as is used to prepare the pharmaceutical compositions of the invention comprising (i) a N-acyl amino acid, (ii) a basic pharmaceutically active compound, and (iii) a pharmaceutically acceptable organic solvent, and the pharmaceutically acceptable organic solvent is simply removed by evaporation. In one embodiment, the pharmaceutically acceptable organic solvent is removed under reduced pressure. Alternatively, the pharmaceutical composition comprising (i) a N-acyl amino acid, (ii) a basic pharmaceutically active compound, and (iii) a pharmaceutically acceptable organic solvent can be diluted with water to provide a solid precipitate and the solid precipitate collected by filtration and, optionally, dried. The resulting solid pharmaceutical composition can optionally be milled to provide smaller particles. Excipients can also be added to the resulting solid pharmaceutical compositions.

The pharmaceutical compositions can be sterilized using an autoclave.

The invention further relates to a method of manufacturing the pharmaceutical composition of the invention.

8.9. Methods of Treating a Condition in an Animal

The invention further relates to a method of treating a condition in an animal. The method comprises administering to an animal in need thereof an effective amount of a pharmaceutically active compound. The pharmaceutical compositions of the invention can be administered by injection or orally.

Solid pharmaceutical compositions can be administered by implanting the solid pharmaceutical composition under the skin of the animal. Solid pharmaceutical compositions, however, may also be administered by injecting an animal with a suspension of the solid pharmaceutical composition in a pharmaceutically acceptable organic solvent.

The pharmaceutical compositions of the invention in the form of a solid, a crystal, a gummy mass or a gel can also be administered orally. For example, encapsulating the pharmaceutical formulations in the form of a solid, a crystal, a gummy mass or a gel in a capsule provides a dosage form that can be administered orally. Furthermore, solid pharmaceutical compositions of the invention can be combined with an excipient such as a binder, diluent, or lubricant and formulated into a tablet to provide a dosage form for oral administration. See, for example, *Remington's Pharmaceutical Sciences*, Alfonso Gennaro ed., 19th ed. 1995), incorporated herein by reference. Oral dosage forms can be designed to release the pharmaceutically active compound in the stomach immediately or almost immediately or to provide sustained release of the pharmaceutically active compound in the stomach. The rate of release of the pharmaceutically active compound is varied by varying the lipophilicity and/or molecular weight of the components of the pharmaceutical composition.

Injectable pharmaceutical compositions are administered to an animal by injecting the animal with the pharmaceutical composition. When the injectable pharmaceutical compositions are injected into an animal, the pharmaceutical compositions form a depot that provides sustained-release of the pharmaceutically active compound. Pharmaceutical compositions that are a suspension of the solid pharmaceutical composition in a pharmaceutically acceptable organic solvent can also form a depot that provides sustained-release of the pharmaceutically active compound when injected into an animal. The components of the pharmaceutical composition, i.e., the amino acid ester or amino acid amide, the carboxylic acid, and the pharmaceutically acceptable organic solvent are biocompatible and non-toxic and, over time, are simply absorbed and/or metabolized by the body. The pharmaceutical compositions of the invention, can also be administered by other routes including, but not limited to, topical, oral, rectal, vaginal, and nasal.

The pharmaceutical compositions of the invention can provide an effective amount of the pharmaceutically active compound to the animal for a period of up to 15 days, and even longer, depending on components of the pharmaceutical composition, i.e., the pharmaceutically active compound or pharmaceutically acceptable salt thereof, the amino acid ester, the carboxylic acid, and the pharmaceutically acceptable organic solvent.

In one embodiment, the pharmaceutical composition provides an effective amount of the pharmaceutically active compound or a pharmaceutically acceptable salt thereof for up to about 3 days.

In one embodiment, the pharmaceutical composition provides an effective amount of the pharmaceutically active compound or a pharmaceutically acceptable salt thereof for up to about 4 days.

In one embodiment, the pharmaceutical composition provides an effective amount of the pharmaceutically active compound or a pharmaceutically acceptable salt thereof for up to about 6 days.

In one embodiment, the pharmaceutical composition provides an effective amount of the pharmaceutically active compound or a pharmaceutically acceptable salt thereof for up to about 8 days.

In one embodiment, the pharmaceutical composition provides an effective amount of the pharmaceutically active compound or a pharmaceutically acceptable salt thereof for up to about 10 days.

In one embodiment, the pharmaceutical composition provides an effective amount of the pharmaceutically active compound or a pharmaceutically acceptable salt thereof for up to about 12 days.

In one embodiment, the pharmaceutical composition provides an effective amount of the pharmaceutically active compound or a pharmaceutically acceptable salt thereof for up to about 15 days.

The pharmaceutical compositions are useful in human medicine and veterinary medicine. The pharmaceutical compositions are particularly useful in veterinary medicine.

In one embodiment, the animal is a human.
In one embodiment, the animal is a cat.
In one embodiment, the animal is a dog.
In one embodiment, the animal is a cow.
In one embodiment, the animal is a pig.
In one embodiment, the animal is a sheep.
In one embodiment, the animal is a horse.

Typically, the pharmaceutical composition further comprising a pharmaceutically acceptable organic solvent are injected in an amount of between about 0.2 mL and 15 mL, preferably between about 0.5 mL and 12 mL, more preferably between about 1 mL and 10 mL. The precise dose to be administered will depend on the seriousness of the condition, and the animal being treated and can be decided according to the judgment of a practitioner and/or each animal's circumstances. Smaller animals typically receive smaller injection volumes. For example, the injection volume for a cat is typically about 1 mL and the injection volume for a dog is typically between about 1 mL and 2 mL. For large animals such as cows and horses, however, the injection volume can be as large as 10 mL and even larger. The amount of the pharmaceutical composition administered to an animal can be determined by standard clinical techniques. In addition, in vitro or in vivo assays can optionally be employed to help identify optimal dosage ranges.

The pharmaceutical composition further comprising a pharmaceutically acceptable organic solvent can be administered, for example, by an intramuscular, intraperitoneal, or subcutaneous injection.

Solid pharmaceutical compositions are typically administered by implanting the solid pharmaceutical compositions containing between about 0.01 and 2 g, preferably between about 0.2 g and 1.5 g, of the pharmaceutically active compound or pharmaceutically acceptable salt thereof under the skin of the animal using methods well known to one of ordinary skill in the art. Solid pharmaceutical compositions can also be administered by injecting a suspension of the solid composition in a solvent. The solid pharmaceutical composition can be suspended in an aqueous solvent or an organic solvent Pharmaceutical compositions for oral administered are typically in the form of a capsule or tablet and typically contain between about 0.001 g and 2 g, preferably between about 0.01 g and 1.5 g, the pharmaceutically active compound or pharmaceutically acceptable salt thereof.

The pharmaceutical compositions of the invention, can also be administered by other routes including, but not limited to, topical, rectal, vaginal, and nasal.

Advantageously, the pharmaceutical compositions, by providing sustained release of the pharmaceutically active compound, have reduced toxicity, particularly in small animal such as cats and dogs. Accordingly, the pharmaceutical compositions of the invention have a better therapeutic profile that conventional immediate release formulations. The methods of the invention, which involve administering a pharmaceutically active compound to an animal by injecting the animal with a pharmaceutical composition of the invention, permit pharmaceutically active compounds to be administered to animals that could, if administered in presently available dosage forms, result in toxicity and even death of the animal being treated. By providing sustained release of the pharmaceutically active compound, the pharmaceutical compositions of the invention need to be administered less frequently and therefore are also easier to administer, more convenient, and more cost effective than conventional modes of administering pharmaceutically active compounds.

8.10 Kits

The invention encompasses kits that can simplify the administration of a pharmaceutically active compound to an animal. A typical kit of the invention comprises a unit dosage form of a pharmaceutical composition of the invention. In one embodiment, the unit dosage form is a container, such as a vial, which can be sterile, containing a pharmaceutical composition of the invention. The kit can further comprise a label or printed instructions instructing the use of the pharmaceutically active compound to treat a condition. In another embodiment, the kit comprises a unit dosage form of a pharmaceutical composition of the invention and a syringe for administering the pharmaceutical composition.

The following examples are set forth to assist in understanding the invention and should not be construed as specifically limiting the invention described and claimed herein. Such variations of the invention, including the substitution of all equivalents now known or later developed, which would be within the purview of those skilled in the art, and changes in formulation or minor changes in experimental design, are to be considered to fall within the scope of the invention incorporated herein.

9. EXAMPLES

9.1 Preparation of Amino Acid Esters

Tryptophan butanoate: 1 g of tryptophan butanoate hydrochloride salt (commercially available from Sigma-Aldrich, St. Louis, Mo. (www.sima-aldrich.com)) was suspended in 25 mL of dichloromethane and 600 µl of triethylamine was added to the suspension with stirring. Stirring was continued for 15 min and the resulting solution was transferred to a separatory funnel. The organic solution was washed twice with 25 mL of water followed by 25 mL of saturated aqueous sodium bicarbonate. The organic layer was then dried over anhydrous sodium sulfate and concentrated under reduced pressure to provide tryptophan butanoate. The structure was confirmed using mass spectroscopy.

Tryptophan octanoate: 4 g of tryptophan butanoate hydrochloride salt (commercially available from Sigma-Aldrich, St. Louis, Mo. (www.sima-aldrich.com)) was suspended in 100 mL of dichloromethane and 3 ml of triethylamine was added to the suspension with stirring. Stirring was continued for 15 min and the resulting solution was transferred to a separatory funnel. The organic solution was washed twice with 25 mL of water followed by 25 mL of saturated aqueous sodium bicarbonate. The organic layer was then dried over anhydrous sodium sulfate and concentrated under reduced pressure to provide tryptophan octanoate. The structure was confirmed using mass spectroscopy.

Tyrosine butanoate: 18.19 g of tyrosine was suspended in a solution of 9.8 g of concentrated sulfuric acid, 40 mL water, 40 mL of butanol, and 200 mL of toluene in a 500 mL round bottom flask equipped with a condenser and a Dean-Stark apparatus. The resulting solution was heated at reflux temperature until no more water could be distilled. The resulting solution was cooled in an ice bath, which caused the solution to separate into two phases. The upper phase was discarded and the lower phase, an oily syrup, was retained. The syrup was mixed with sufficient 5% aqueous sodium bicarbonate solution to neutralize acidic impurities to provide a solid that was collected by filtration and washed with cold water. The resulting solid was re-crystallized in ethyl acetate.

Isoleucine butyrate: 26.23 g of isoleucine was dissolved in a solution of 20 g of concentrated sulfuric acid, 20 mL water, 40 mL of butanol, and 200 mL of toluene in a 500 mL round bottom flask equipped with a condenser and a Dean-Stark apparatus. The resulting solution was heated at reflux temperature until no more water could be distilled. The resulting solution was then cooled to room temperature and washed with saturated aqueous sodium bicarbonate to neutralize acidic impurities, washed with saturated brine, and dried over anhydrous sodium sulfate. The solvent was removed under reduced pressure and the resulting liquid distilled under vacuum to provide isoleucine butyrate as a colorless liquid.

Phenylalanine butyrate: 16.52 g of isoleucine was dissolved in a solution of 10 g of concentrated sulfuric acid, 20 mL water, 20 mL of butanol, and 200 mL of toluene in a 500 mL round bottom flask equipped with a condenser and a Dean-Stark apparatus. The resulting solution was heated at reflux temperature until no more water could be distilled. The resulting solution was then cooled to room temperature and washed with saturated aqueous sodium bicarbonate to neutralize acidic impurities, washed with saturated brine, and dried over anhydrous sodium sulfate. The solvent was removed under reduced pressure and the resulting liquid distilled under vacuum to provide phenylalanine butyrate.

Phenylalanine octanoate: 16.52 g of phenylalanine was dissolved in a solution of 10 g of concentrated sulfuric acid, 20 mL water, 20 mL of octanol, and 120 mL of toluene in a 500 mL round bottom flask equipped with a condenser and a Dean-Stark apparatus. The resulting solution was heated at reflux temperature until no more water could be distilled. The resulting solution was then cooled to room temperature and washed with saturated aqueous sodium bicarbonate to neutralize acidic impurities, washed with saturated brine, and dried over anhydrous sodium sulfate. The solvent was then removed under reduced pressure to provide phenylalanine octanoate as a white solid that was purified using a silica gel column eluted with a 1:9 methanol:dichloromethane mixture.

Phenylalanine dodecanoate: 16.52 g of phenylalanine was dissolved in a solution of 10 g of concentrated sulfuric acid, 20 mL water, 20 mL of dodecanol, and 120 mL of toluene in a 500 mL round bottom flask equipped with a condenser and a Dean-Stark apparatus. The resulting solution was heated at reflux temperature until no more water could be distilled. The resulting solution was then cooled to room temperature and washed with saturated aqueous sodium bicarbonate to neutralize acidic impurities, washed with saturated brine, and dried over anhydrous sodium sulfate. The solvent was then removed under reduced pressure to provide phenylalanine dodecanoate as a solid that was purified using a silica gel column eluted with a 1:9 methanol:dichloromethane mixture.

Tyrosine octanoate: 9.06 g of tyrosine was dissolved in a solution of 10 g of concentrated sulfuric acid, 20 mL water, 10 mL of octanol, and 200 mL of toluene in a 500 mL round bottom flask equipped with a condenser and a Dean-Stark apparatus. The resulting solution was heated at reflux temperature until no more water could be distilled. The resulting solution was then cooled to room temperature and washed with saturated aqueous sodium bicarbonate to neutralize acidic impurities to provide an emulsion. About 150 mL of ethylacetate was added to the emulsion to provide two phases. The aqueous phase was discarded and the organic phase washed with saturated Brine and dried over anhydrous sodium sulfate. The solvent was the removed under reduced pressure to provide tyrosine octanoate as a white solid that was purified using a silica gel column eluted with a 1:9 methanol:dichloromethane mixture.

Isoleucine octanoate: 13.1 g of isoleucine was dissolved in a solution of 10 g of concentrated sulfuric acid, 20 mL water, 20 mL of octanol, and 200 mL of toluene in a 500 mL round bottom flask equipped with a condenser and a Dean-Stark apparatus placed in an oil bath. The resulting solution was heated at reflux temperature until no more water could be distilled. The resulting solution was then cooled to room temperature, diluted with 120 mL of ethyl acetate and the organic layer washed with saturated aqueous sodium bicarbonate to neutralize acidic impurities, washed with saturated Brine, and dried over anhydrous sodium sulfate. The solvent was removed under reduced pressure and the resulting liquid distilled to provide isoleucine octanoate as a colorless liquid.

Proline butanoate: 34.5 g of proline was suspended in a solution of 35 g of concentrated sulfuric acid, 40 mL water, 120 mL of butanol, and 200 mL of toluene in a 500 mL round bottom flask equipped with a condenser and a Dean-Stark apparatus. The resulting solution was heated at reflux temperature until no more water could be distilled. The resulting solution was then cooled to room temperature, washed with saturated aqueous sodium bicarbonate to neutralize acidic impurities, washed with saturated Brine, and dried over anhydrous sodium sulfate. The solvent was removed under reduced pressure and the resulting liquid distilled to provide proline butanoate as a colorless liquid.

9.2 Pharmaceutical Compositions Containing Flunixin and an Amino Acid Ester

Compositions containing a salt of flunixin and tryptophan octanoate: 1.5 g of flunixin and 1.766 g of tryptophan octanoate were weighed into a 10 mL volumetric flask. 0.5 mL of propylene glycol was added to the flack and the flask filled to about 90% of the volume with glycerol formal. The flask was then placed on a shaker and shaken with occasional sonication over a period of about 30 min to provide a clear solution. The flask was then filled to volume of 10 mL with glycerol formal. When 1 mL of the pharmaceutical composition is injected into 5 mL of water, a precipitate is observed to form.

Compositions containing a salt of flunixin and tryptophan butanoate: 0.75 g of flunixin and 0.73 g of tryptophan butanoate were weighed into a 5 mL volumetric flask. 0.25 mL of propylene glycol was added to the flask and the flask filled to about 90% of the volume with glycerol formal. The flask was then placed on a shaker and shaken with occasional sonication over a period of about 30 min to provide a clear solution. The flask was then filled to volume of 5 mL with glycerol formal. When 1 mL of the pharmaceutical composition is injected into 5 mL of water, a precipitate is observed to form.

A solution of fee flunixin (i.e., not as a salt) was also prepared by weighing 1.5 g of flunixin into a 10 mL volumetric flask and filling the flask to about 90% of the volume with N-methylpyrrolidone. The flask was then placed on a shaker and shaken with occasional sonication over a period of about 10 min to provide a clear solution. The flask was then filled to volume a volume of 10 mL with N-methylpyrrolidone. When 1 mL of the pharmaceutical composition is injected into 5 mL of water, a precipitate is observed to form.

In vitro release of flunixin from the flunixin containing pharmaceutical compositions: 1 mL aliquots of each of the above flunixin compositions were sealed in a dialysis bag (commercially available from Pierce Biotechnology, Inc. of Rockford Ill.) and the dialysis bag suspended in flasks containing 150 mL of phosphate buffered saline at pH 7.4. When the dialysis bag is suspended into the flask containing phosphate buffered saline, a precipitate was observed to form in the dialysis bag. Aliquots of saline were then removed at various intervals and the concentration of flunixin determined using high pressure liquid chromatography (HPLC).

For HPLC analysis 100 μL was injected on a Phenomenex Luna 5:M phenyl-hexyl 100A, 250×4.6 mm analytical column operated at a flow rate of 1.7 mL/min. The HPLC was interfaced to a UV detector operated at 285 nm. The HPLC column was eluted using gradient elution according to the following profile:

| Time | Percent Pump A | Percent Pump B |
|------|---------------|---------------|
| 0    | 30            | 70            |
| 10.5 | 85            | 15            | wherein the solvent in pump A was 25 mM phosphate buffer at pH 2.4 and the solvent in pump B was acetonitrile. The total run time was 25 min. The serum concentration of flunixin was then determined by comparing the area under the curve for the HPLC peak corresponding to flunixin to a standard curve of peak areas v. known concentrations of flunixin in phosphate-buffered saline. The standard curve was prepared using the following concentrations of flunixin 4, 2, 1, 0.5, and 0 g/mL.

FIG. 1 shows the percent of flunixin released as a function of time for each of the flunixin formulations. (▲) represents the percent of flunixin released from the composition containing the salt of flunixin and tryptophan octanoate, (■) represents the percent of flunixin released from the composition containing the salt of flunixin and tryptophan butanoate, and (♦) represents the percent of flunixin released from the composition containing free flunixin dissolved in N-methylpyrrolidone.

The results depicted in FIG. 1 show that the flunixin compositions of the invention release flunixin into saline at a substantially slower rate than a composition containing free flunixin. The results also demonstrate that by varying the amino acid ester, the rate of release of flunixin can be modulated. The data depicted in FIG. 1 show that flunixin is released more slowly from tryptophan octanoate than from tryptophan butanoate. Tryptophan octanoate is more lipophilic than tryptophan butanoate.

Example 9.3

Administration of Flunixin to Dogs

Two dogs were injected with commercially available flunixin (Banamine®, commercially available from Schering-Plough Animal Health, Omaha, Nebr.) at a dose of 8 mg/kg.

Four dogs were injected with the composition of Example 9.2 containing the salt of flunixin and tryptophan octanoate in propylene glycol and glycerol formal at a dose of 8 mg/kg.

Blood was withdrawn from each dog at various time intervals and the serum concentration of flunixin determined by the following procedure:

(i) A Strata X-C 33 μm Cation Mixed-Mode Polymer 30 mg/mL cartridge was condition by washing with 1 mL of methanol and 1 mL of deionized water using gravity flow;

(ii) 1 mL of serum acidified with 20 μl of phosphoric acid was applied to the conditioned cartridge;

(iii) The column was washed with 1 mL of 0.1% $H_3PO_4$/$H_2O$, 1 mL of acetonitrile, and 2 mL of methanol;

(iv) The column was eluted with 4 mL ammonia in methanol (15% of 2M $NH_4OH$ in methanol);

(v) The solvent was removed from the eluant using a stream of nitrogen gas; and (vi) The resulting residue was then reconstituted with 1 mL of 50:50 methanol/50 mM phosphate buffer at pH 2.3 and analyzed by HPLC using the HPLC method described in Example 9.2.

Figure 2:
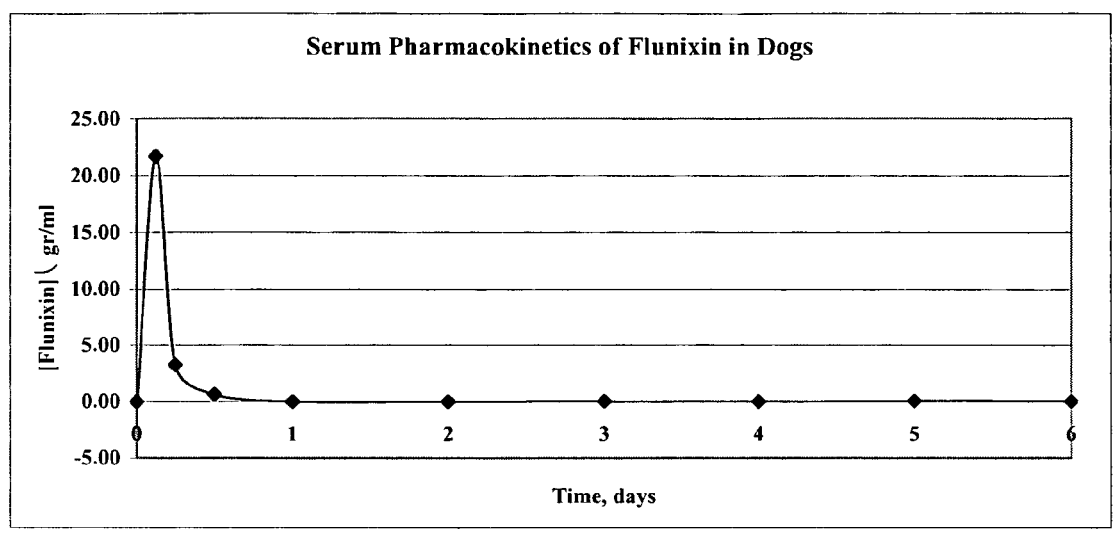
FIG. 2 depicts the average serum concentration of flunixin as a function of time for two dogs administered Banamine® at a dose of 8 mg/kg.

FIG. 2 depicts the average serum concentration of flunixin as a function of time for the two dogs administered Banamine®.

Figure 3:
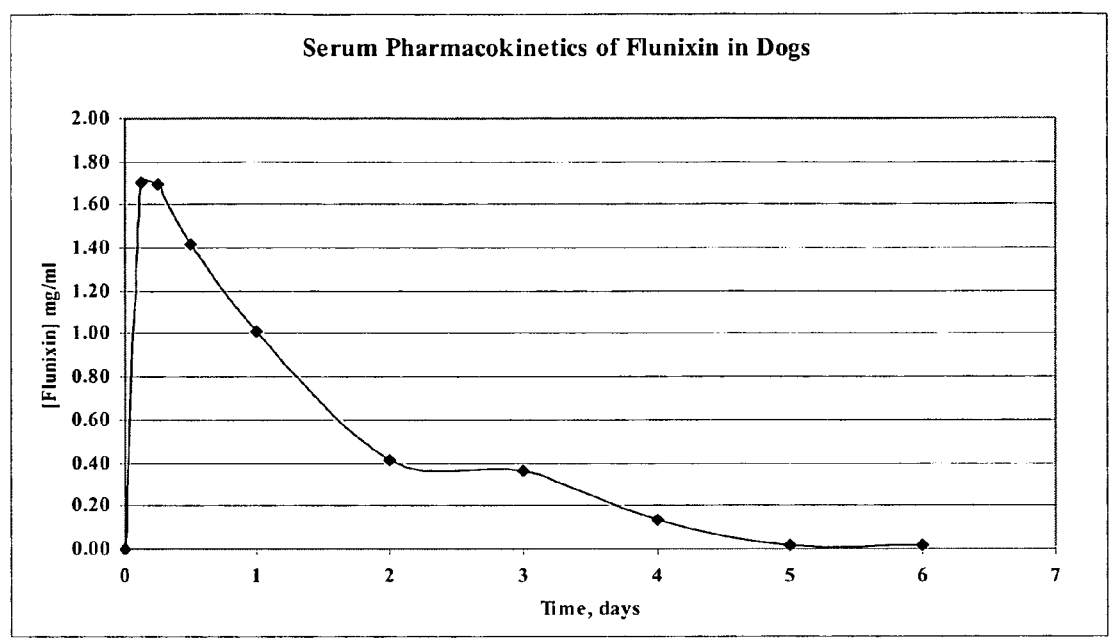
FIG. 3 depicts the average serum concentration of flunixin as a function of time for four dogs administered a composition of the invention containing a salt of flunixin and tryptophan octanoate in propylene glycol and glycerol formal, prepared as described in Example 9.2, at a dose of 8 mg/kg.

FIG. 3 depicts the average serum concentration of flunixin as a function of time for the four dogs administered the composition of Example 9.2 containing the salt of flunixin and tryptophan octanoate propylene glycol and glycerol formal.

The results depicted in FIG. 2 and FIG. 3 show that by using the compositions of the invention it is possible to maintain an effective serum level of flunixin for a longer length of time than is possible using a commercially available formulations of flunixin (Banamine®, commercially available from Schering-Plough Animal Health, Omaha, Nebr.).

Example 9.4

Preparation of N-acyl Amino Acids

Phenylalanine butyramide: 5 g of phenylalanine was added to 20 mL of butyric anhydride and the resulting mixture heated to about 100° C. for about 3 h. Excess butyric anhydride was then removed under reduced pressure to provide a solid residue that was recrystallized from ethanol to provide phenylalanine butyramide.

Example 9.5

Compositions Comprising a Phosphorylated Nucleotide

Adenosine monophosphate (AMP) is used as a model for a phosphorylated nucleotide.

Compositions containing a salt of AMP and isoleucine butyrate: 1.2 g of isoleucine butyrate and 1 g of AMP were weighed into a 10 mL volumetric flask and the volumetric flask filled to about 90% of the volume with glycerol formal. The flask was shaken to dissolve the AMP isoleucine butyrate and then the flask was filled to volume with glycerol formal. 1 eq. of a phosphorylated nucleotide such as adefovir can be substituted for each eq. of AMP. 1 g of AMP alone, i.e., in the absence of isoleucine butyrate, will not dissolve in 10 mL of glycerol formal.

Compositions containing a salt of AMP and isoleucine butyrate and a salt of decanoic acid and isoleucine butyrate: 1 g of AMP, 0.99 g of decanoic acid, and 2.4 g of isoleucine butyrate were weighed into a 10 mL volumetric flask and the volumetric flask filled to about 90% of the volume with glycerol formal. The flask was shaken to dissolve the AMP, decanoic acid, and isoleucine butyrate and then the flask was filled to volume with glycerol formal. 1 eq. of a phosphorylated nucleotide such as adefovir can be substituted for each eq. of AMP.

Compositions containing a salt of AMP and tyrosine butyrate: 0.682 g of tyrosine butyrate and 0.5 g of AMP were weighed into a 10 mL volumetric flask and the volumetric flask filled to about 90% of the volume with N-methylpyrrolidone. The flask was sonicated for about 30 min to dissolve the AMP and tyrosine butyrate and then the flask was filled to volume with N-methylpyrrolidone. 1 eq. of a phosphorylated nucleotide such as adefovir can be substituted for each eq. of AMP. 0.5 g of AMP alone, i.e., in the absence of tyrosine butyrate, will not dissolve in 10 mL of N-methyl pyrrolidone.

Compositions containing a salt of AMP and phenylalanine dodecanoate: 1 g of phenylalanine dodecanoate and 0.347 g of AMP were weighed into a 10 mL volumetric flask and the volumetric flask filled to about 90% of the volume with N-methyl pyrrolidone. The flask was sonicated for about 30 min to suspend the AMP and phenylalanine dodecanoate and the flask was filled to volume with N-methylpyrrolidone. The flask was then shaken to provide an injectable composition of a suspension of AMP and phenylalanine dodecanoate. 1 eq. of a phosphorylated nucleotide such as adefovir can be substituted for each eq. of AMP.

Compositions containing a salt of AMP and 2.1 equivalents of the ester made from lysine and a $C_{16}$ straight chain alcohol (i.e., $CH_3(CH_2)_{14}CH_2$—OH): 45 mg of AMP and 96 mg of the lysine ester were suspended in about 2 mL of glycerol formal. The resulting suspension was placed in a sonic bath and shaken and to provide a clear solution. The volume of the solution was made up to a volume of 3 mL. The resulting solution contains the salt of AMP at a concentration of about 1.5% (w/v). When 1 mL of the pharmaceutical composition is injected into 5 mL of water, a precipitate is observed to form.

Compositions containing a salt of AMP and 2.1 equivalents of the ester made from lysine and a $C_{16}$ straight chain alcohol (i.e., $CH_3(CH_2)_{14}CH_2$—OH): 150 mg of AMP and 320 mg of the lysine ester were suspended in about 2 mL of glycerol formal. The resulting suspension was placed in a sonic bath and shaken and to provide a clear solution. The volume of the solution was made up to a volume of 3 mL. The resulting solution contains the salt of AMP at a concentration of about 5% (w/v). When 1 mL of the pharmaceutical composition is injected into 5 mL of water, a precipitate is observed to form.

Compositions containing a salt of AMP and 6.6 equivalents of the ester made from lysine and a $C_{16}$ straight chain alcohol (i.e., $CH_3(CH_2)_{14}CH_2$—OH): 150 mg of AMP and 1.92 g of the lysine ester were suspended in about 2 mL of glycerol formal. The resulting suspension was placed in a sonic bath and shaken and to provide a clear solution. The volume of the solution was made up to a volume of 3 mL. The resulting solution contains the salt of AMP at a concentration of about 5% (w/v). When 1 mL of the pharmaceutical composition is injected into 5 mL of water, a precipitate is observed to form.

Example 9.6

Pharmaceutical Composition Comprising Isoleucine Butyrate, Lauric Acid, and Terbinafine A: Terbinafine (5 g), lauric acid (7.56 g), and isoleucine butyrate (3.54 g) were suspended in about 15 mL of glycerol formal in a 25 mL volumetric flask. The resulting suspension was then sonicated to provide a clear solution. Propylene glycol (1.5 mL) was added and the resulting solution mixed well. The volumetric flask was then filled to a volume of 25 mL with glycerol formal to provide a clear solution. The resulting pharmaceutical composition contains 20% (w/v) terbinafine as the lauric acid salt. The pharmaceutical composition also contains the salt formed between lauric acid and isoleucine butyrate. When 1 mL of the pharmaceutical composition is injected into 5 mL of water, a precipitate is observed to form.

B: As a comparison, another pharmaceutical composition was prepared that does not include the salt formed between lauric acid and isoleucine butyrate. The composition was prepared by suspending terbinafine (5 g) and lauric acid (1.1 eq.) in about 15 mL of glycerol formal in a 25 mL volumetric flask and sonicating the resulting solution to provide a clear solution. Propylene glycol (1.5 mL) was added and the resulting solution mixed well. The volumetric flask was then filled to a volume of 25 mL with glycerol formal to provide a clear solution. The resulting pharmaceutical composition contains 20% (w/v) terbinafine as the lauric acid salt. When 1 mL of the pharmaceutical composition is injected into 5 mL of water, a precipitate is observed to form.

Example 9.7

Administration of Terbinafine to Dogs

Three dogs (dogs A, B, and C) were administered the pharmaceutical composition of Example 9.6 A at a dose of 20 mg/kg by subcutaneous injection in the neck.

Three other dogs (dogs D, E, and F) were administered the pharmaceutical composition of Example 9.6 B at a dose of 20 mg/kg by subcutaneous injection in the neck.

Three other dogs (dogs G, H, and I) were orally administered a commercially available 250 mg terbinafine tablet (commercially available as Lamisil Tablets® from Novartis Pharmaceutical Corporation of New Jersey) once per day for 6 days.

Serum samples were obtained from each dog at 0, 1, 12, 24, 48, 72, and 168 hours and subjected to solid phase extraction, described below, and then analyzed by HPLC using the HPLC method described below. Also, 7 days after injection, a skin biopsy was taken of the right, left, and center of the dorsoscapular region of each dog and the tissue analyzed for terbinafine as described below. For the dogs administered terbinafine by injection, the injection site was monitored by a veterinarian for adverse reaction.

Tissue Preparation:
1. Mince tissue thoroughly.
2. Place about 5 mg of minced tissue in a vial and add 10 mL of methanol.
3. Add 200 µL of phosphoric acid to the resulting methanol solution.
4. Cool the methanol solution in an ice bath to minimize heating and then homogenize the methanol solution for about 1 min.
5. Ultrasonicate the methanol solution for about 20 seconds.
6. Homogenize the methanol solution for about 1 min.
7. Ultrasonicate the methanol solution for about 20 seconds.
8. Centrifuge the methanol solution at about 4° C. and about 8250 rcf for about 30 min.
9. Decant the resulting supernatant into a separate vial to avoid mixing pellet back into the supernatant during solid phase extraction.
10. Perform solid phase extraction as described below on the supernatant.

Solid Phase Extraction of Serum or Supernatant:
1. Condition a Strata 30 mg/1 mL X-C cartridge (commercially available from Mallinckrodt Baker, Inc. of Phillipsburg, N.J.) with 1 mL of methanol and 2 mL of deionized water using gravity flow.
2. Apply 1 mL of serum (or supernatant) acidified with 20 µL of phosphoric acid to the conditioned cartridge.
3. Wash the cartridge with 1 mL 0.1% $H_3PO_4/H_2O$, 1 mL acetonitrile, and 1 mL of methanol.
4. Elute the cartridge with 1850 µL of 15% diethylamine in methanol into a 2 mL volumetric flask.
5. Fill the volumetric flask to 2 mL with 15% diethylamine.
6. Add 1000 µL of 50% phosphoric acid to the 2 mL volumetric flask and vortex the resulting mixture.
7. Filter the resulting solution into a vial.
8. Analyze the resulting solution for terbinafine using the HPLC method described below.

Analysis of Terbinafine by HPLC:
Column: Phenomenex Lunar® 5µ, C8, 100 Å, 250 mm×4.6 mm (commercially available from Phenomenex of Torrance, Calif.).
Mobile Phase: 40% 25 mM Phosphate Buffer pH 2.4 60% Methanol
Elution Profile: Isocratic.
Detection: UV, 223 nm
Temperature: Ambient
Injection: 100 µL
Run Time: 20 min, isocratic.
Flow rate: 1 mL/min
Limit of detection: about 8 ng/mL
Limit of quantitation: about 75 ng/mL The concentration of terbinafine was determined by comparing the area under the curve for the HPLC peak corresponding to terbinafine to a standard curve of peak area v. known concentrations of terbinafine. The standard curve was obtained by:

1. Prepare a standard stock solution at a concentration of 1 mg/mL of terbinafine in methanol by weighing 100 mg of terbinafine into a 100 mL volumetric flask and diluting to volume.
2. Prepare the following serum spiking solutions:
    Solution A: 400 µL standard stock solution+600 µL methanol=400 µg/mL of terbinafine
    Solution B: 200 µL standard stock solution+800 µL methanol=200 µg/mL of terbinafine
    Solution C: 100 µL standard stock solution+900 µL methanol=100 µg/mL of terbinafine
    Solution D: 50 µL standard stock solution+950 µL methanol=50 µg/mL of terbinafine
    Solution E: 10 µL standard stock solution+990 µL methanol=10 µg/mL of terbinafine
    Solution F: 0 µL standard stock solution+1000 µL methanol=0 µg/mL of terbinafine
3. Prepare the following standard serum solutions:
    a. 15 µL Solution A+1485 µL serum=4 µg/mL of terbinafine.
    b. 15 µL Solution B+1485 µL serum=2 µg/mL of terbinafine.
    c. 15 µL Solution C+1485 µL serum=1 µg/mL of terbinafine.
    d. 15 µL Solution D+1485 µL serum=0.5 µg/mL of terbinafine.
    e. 15 µL Solution E+1485 µL serum=0.1 µg/mL of terbinafine.
    f. 15 µL Solution E+1485 µL serum=0 µg/mL of terbinafine.

Each of the above standard serum solutions is analyzed using the HPLC method described above to generate a standard curve. The following peak areas were obtained for each of the standard serum solutions:

| Terbinafine Concentration (µg/mL) | HPLC Area |
| --- | --- |
| 0.1 | 59.92624 |
| 0.5 | 279.6904 |

-continued

| Terbinafine Concentration (μg/mL) | HPLC Area |
|---|---|
| 1.0 | 566.0115 |
| 2.0 | 1073.03 |
| 4.0 | 2214.295 |

A positive control (to demonstrate that the analysis is capable of detecting terbinafine) is prepared by adding 1 mL of 15% diethylamine in methanol to a 2 mL volumetric flask followed by 10 μL of Solution A and filling the volumetric flask to volume with 15% diethylamine in methanol. To the resulting solution is then added 1 mL of 50% phosphoric acid and the resulting solution mixed using a vortex mixer. The resulting positive control has a terbinafine concentration of 4 μg/mL. A positive control having a concentration of 0.5 μg/mL can be made following the same procedure except using 10 μL of Solution D.

A negative control (to demonstrate that the no other compounds co-elute with terbinafine) is prepared by mixing 2 mL of 15% diethylamine in methanol with 1 mL of 50% phosphoric acid in a test tube and mixing the resulting solution using a vortex mixer for about 10 sec.

The average concentration of terbinafine in the serum of each group of dogs was determined as described above and is provided below in Table I:

TABLE I

| | Average Serum Concentration of Terbinafine | | |
|---|---|---|---|
| Time (hours) | Dogs A, B, and C | Dogs D, E, and F | Dogs G, H, and I |
| 0 | 0.00 | 0.00 | 0.00 |
| 1 | 0.02 | 0.01 | 2.36 |
| 12 | 0.12 | 0.02 | 0.08 |
| 24 | 0.27 | 0.02 | 0.46 |
| 48 | 0.05 | 0.02 | 0.25 |
| 72 | 0.17 | 0.01 | 0.85 |
| 168 | 0.05 | 0.12 | 3.23 |

It is known that terbinafine can be toxic at high systemic and tissue concentrations. The results show that administering a single injection of the pharmaceutical composition of the invention provides a serum level of terbinafine over a period of 7 days that is less than when terbinafine is orally administered once daily as a commercially available tablet. The pharmaceutical compositions of the invention, however, provide a serum level of terbinafine that is physiologically relevant for the intended therapeutic effect.

The pharmaceutical composition of the invention containing terbinafine as the lauric acid salt and the salt formed between lauric acid and isoleucine butyrate provides a lower level of terbinafine in the serum than terbinafine administered orally once per day for 6 days as a 250 mg tablet. Accordingly, administering terbinafine using the pharmaceutical composition of the invention is less toxic than orally administered terbinafine.

Visually inspection of the injection site for the dogs administered terbinafine by injection i.e., dogs A, B, and C and dogs D, E, and F, by a veterinarian indicated that the dogs administered the pharmaceutical composition of Example 9.6 A containing terbinafine as the lauric acid salt and also containing the salt formed between lauric acid and isoleucine butyrate (i.e., dogs A, B, and C) showed less swelling and irritation at the injection site than the dogs that were administered the pharmaceutical composition of Example 9.6 B containing terbinafine as the lauric acid salt (i.e., dogs D, E, and F). These results show that the pharmaceutical composition containing the salt formed between lauric acid and isoleucine butyrate in combination with terbinafine as the lauric acid salt is less irritating than a pharmaceutical composition that contains only terbinafine as the lauric acid salt when administered by subcutaneous injection.

The tissue concentration of terbinafine was also determined for each of the dogs and is provided below in Table II.

TABLE II

| | Tissue Concentration of Terbinafine in Tissue Obtained From the Right, Left, and Center of the Dorsoscapular Region (μg/g) | | |
|---|---|---|---|
| Dog | Center | Left | Right |
| A | 31.34 | — | 222.5[a] |
| B | 19.74 | 27.43 | 38.40 |
| C | 20.17 | 15.38 | 28.14 |
| Average | 24.72 | 21.40 | 96.36 |
| | | | (33.27)[b] |
| D | 29.54 | 26.64 | 20.08 |
| E | 16.42 | 19.26 | 141.61 |
| F | 45.43 | 31.48 | 34.82 |
| Average | 30.49 | 25.79 | 65.50 |
| G | 97.24 | 117.52 | 108.23 |
| H | 121.57 | 73.68 | 72.80 |
| I | 46.79 | 33.47 | 38.11 |
| Average | 88.53 | 74.89 | 73.05 |

[a]Value appears to be in error, although the source of the error is unclear.
[b]If the value of 222.5 μg/g for dog A is eliminated, the average value is 33.27 μg/g.

As discussed above, it is known that terbinafine can be toxic at high systemic and tissue concentrations. The results show that administering a single injection of the pharmaceutical composition of the invention provides a tissue concentration of terbinafine over a period of 7 days that is less than when terbinafine is orally administered once daily as a commercially available tablet. The pharmaceutical compositions of the invention, however, provide a tissue concentration of terbinafine that is physiologically relevant for the intended therapeutic effect.

The present invention is not to be limited in scope by the specific embodiments disclosed in the examples which are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims.

A number of references have been cited, the entire disclosure of which are incorporated herein by reference.

What is claimed is:

1. An injection composition comprising
   (i) a salt formed between
   (a) an amino acid ester of formula I:

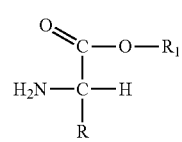

(I)

wherein
R is the amino acid side chain; and
$R_1$ is a $C_1$ to $C_{22}$ hydrocarbon group or
amino acid amide of formula (II):

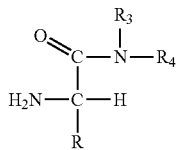 (II)

wherein
R is the amino acid side chain;
$R_3$ is a $C_1$ to $C_{22}$ hydrocarbon group; and
$R_4$ is hydrogen or a $C_1$ to $C_{22}$ hydrocarbon group, and
(b) an acidic pharmaceutically active compound; and
(ii) a pharmaceutically acceptable organic solvent;
formulated to be administered to an animal by injection,
wherein
the composition is substantially free of water,
the composition is injectable and forms a precipitate when injected into water, and
the composition, when administered to an animal by injection, forms a depot that releases the pharmaceutically active compound over time.

2. The composition of claim 1, wherein the amino acid ester or amino acid amide is an ester or amide of an amino acid selected from the group consisting of glycine, alanine, valine, leucine, isoleucine, phenylalanine, asparagine, glutamine, tryptophane, proline, serine, threonine, tyrosine, hydroxyproline, cysteine, methionine, aspartic acid, glutamic acid, lysine, arginine, and histidine.

3. The composition of claim 1, wherein the amino acid ester is obtained by esterifying an amino acid with a straight or branched chain, saturated or unsaturated alkyl alcohol.

4. The composition of claim 3, wherein the alkyl alcohol is a $C_1$ to $C_{22}$ alcohol.

5. The composition of claim 4, wherein $C_1$ to $C_{22}$ alcohol is selected from the group consisting of, methanol, ethanol, propanol, butanol, pentanol, hexanol, heptanol, octanol, nonanol, decanol, undecanol, dodecanol, tridecanol, tetradecanol, pentadecanol, hexadecanol, heptadecanol, octadecanol, allyl alcohol, cyclopentanol, cyclohexanol, cis-9-hexadecenanol, cis-9-octadecenanol, cis, cis-9,12-octadecenanol, and cis, cis, cis-9, 12,15-octadecatrienanol.

6. The composition of claim 1, wherein the acidic pharmaceutically active compound is selected from the group consisting of aspirin, flunixin, diclofenac, naproxen, ketoprofen, carprofen, and ibuprofen.

7. The composition of claim 1, wherein acidic pharmaceutically active compound is a phosphorylated nucleotide.

8. The composition of claim 7, wherein the nucleotide is adefovir.

9. The composition of claim 1, wherein the solvent is selected from the group consisting of pyrrolidone, N-methyl-2-pyrrolidone, polyethylene glycol, propylene glycol, glycerol formal, isosorbid dimethyl ether, ethanol, dimethyl sulfoxide, tetraglycol, tetrahydrofurfuryl alcohol, triacetin, propylene carbonate, dimethyl acetamide, dimethyl formamide, dimethyl sulfoxide, and combinations thereof.

10. The composition of claim 1, wherein the molar ratio of acidic groups on the acidic pharmaceutically active compound to the amino acid ester ranges from about 1.5:1 to 1:1.

11. The composition of claim 1, wherein the molar ratio of acidic groups on the acidic pharmaceutically active compound to the amino acid ester is about 1:1.

12. The composition of claim 1, wherein the combined amount of the acidic pharmaceutically active compound and the amino acid ester is present in an amount ranging from about 1 to 90 percent by weight of the pharmaceutical composition.

13. The composition of claim 1, wherein the combined amount of the acidic pharmaceutically active compound and the amino acid ester is present in an amount ranging from about 10 to 60 percent by weight of the pharmaceutical composition.

14. The composition of claim 1, wherein the pharmaceutically active compound is flunixin and the amino acid ester is tryptophan octanoate or tryptophan butanoate.

15. The composition of claim 1, wherein the pharmaceutically acceptable organic solvent is about 5% propylene glycol in glycerol formal.

16. The composition of claim 1, comprising an amino acid ester, wherein $R_1$ is a $C_{10}$-$C_{18}$ hydrocarbon group.

17. The composition of claim 1, comprising an amino acid amide of formula (II).

* * * * *